United States Patent
Xue et al.

(10) Patent No.: US 11,834,716 B2
(45) Date of Patent: Dec. 5, 2023

(54) METHOD FOR PREDICTING RESPONSE OF ESOPHAGUS CANCER TO ANTI-ERBB3 ANTIBODY THERAPY, AND KIT

(71) Applicant: CANBRIDGE LIFE SCIENCES LTD, Beijing (CN)

(72) Inventors: James Qun Xue, Beijing (CN); Jing Wang, Beijing (CN); Ya Gao, Beijing (CN); Huaizhong Hu, Beijing (CN)

(73) Assignee: Canbridge Life Sciences LTD, Beijing (CN)

( * ) Notice: Subject to any disclaimer, the term of this patent is extended or adjusted under 35 U.S.C. 154(b) by 671 days.

(21) Appl. No.: 16/626,147

(22) PCT Filed: Jun. 12, 2018

(86) PCT No.: PCT/CN2018/090790
§ 371 (c)(1),
(2) Date: Dec. 23, 2019

(87) PCT Pub. No.: WO2018/233511
PCT Pub. Date: Dec. 27, 2018

(65) Prior Publication Data
US 2021/0025006 A1 Jan. 28, 2021

(30) Foreign Application Priority Data
Jun. 22, 2017 (CN) .......................... 201710485107.3

(51) Int. Cl.
*C12Q 1/6886* (2018.01)
*G01N 33/574* (2006.01)
*C07K 16/32* (2006.01)

(52) U.S. Cl.
CPC ............ *C12Q 1/6886* (2013.01); *C07K 16/32* (2013.01); *G01N 33/57407* (2013.01);
(Continued)

(58) Field of Classification Search
CPC ............ C12Q 1/6886; C12Q 2600/106; C12Q 2600/158
See application file for complete search history.

(56) References Cited

U.S. PATENT DOCUMENTS

| 8,481,687 B2 * | 7/2013 | Vincent ................... A61P 35/00 530/387.3 |
| 9,828,635 B2 | 11/2017 | Vincent et al. |
| 2005/0095634 A1 | 5/2005 | Baker et al. |

FOREIGN PATENT DOCUMENTS

| CN | 103959065 | 7/2014 |
| CN | 103959065 A | 7/2014 |
| CN | 106692969 | 5/2017 |

OTHER PUBLICATIONS

Zhang, N. et al. Acta Biochim. Biophys. Sin. 48(1):39-48. (2016; online Oct. 24, 2015). (Year: 2015).*

(Continued)

*Primary Examiner* — Diana B Johannsen
(74) *Attorney, Agent, or Firm* — Dority & Manning, P.A.

(57) ABSTRACT

Disclosed is a method for predicting whether esophageal cancer is sensitive or resistant to treatment with an ERBB3 inhibitor, e.g., an anti-ERBB3 antibody. Specifically, the method predicts by measurement of expression at the RNA level, or at the protein level, of at least one biomarker selected from SDC2, PTGES, NCF2, NOXA1, CARD6 and GNAZ in a tumor sample.

9 Claims, 10 Drawing Sheets

Specification includes a Sequence Listing.

(52) U.S. Cl.
CPC ... *G01N 33/57484* (2013.01); *C07K 2317/56* (2013.01); *C07K 2317/565* (2013.01); *C12Q 2600/106* (2013.01); *C12Q 2600/158* (2013.01); *G01N 2333/485* (2013.01)

(56) References Cited

OTHER PUBLICATIONS

Huang, X. et al. Oncology Reports 21:1123-1129. (Year: 2009).*
Meetze, K. et al. Clinical Cancer Research 21(5):1106. (Year: 2015).*
De Oliveira, T. et al. Molecular Cancer 11:19. (Year: 2012).*
International Search Report and English Translation thereof, PCT Application No. PCT/CN2018/090790, dated Dec. 27, 2018, 7 pages.
Ausubel, et al. "Ch. 19: Informatics for Molecular Biologists" *Curr. Protoc. Molec. Biol.* 33(1) (1996) pp. 19.0.3-19.0.4.
Biomarkers Definitions Working Group, et al. "Biomarkers and surrogate endpoints: Preferred definitions and conceptual framework" *Clin. Pharmacol. Ther.* 69(3) (2001) pp. 89-95.
Cho, W.C.S. "OncomiRs: the discovery and progress of microRNAs in cancers" *Molecul. Canc.* 6:60 (2007) pp. 1-7.
Clark-Langone, et al. "Biomarker discovery for colon cancer using a 761 gene RT-PCR Assay" *BMC Genomics* 8:279 (2007) pp. 1-18.
Engelman, et al. "The Role of the ErbB Family Members in Non-Small Cell Lung Cancers Sensitive to Epidermal Growth Factor Receptor Kinase Inhibitors" *Clin. Canc. Res.* 12(14 Suppl) (2006) pp. 4372s-4376s.
Meetze, et al. "Neuregulin 1 Expression Is a Predictive Biomarker for Response to AV-203, an ERBB3 Inhibitory Antibody, in Human Tumor Models" *Clin. Canc.* Res. 21(5) (2015) pp. 1106-1114.
Pepe, M.S. "The Statistical Evaluation of Medical Tests for Classification and Prediction" *Book Rev.* (2003) p. 656.
Ritter, et al. "Human Breast Cancer Cells Selected for Resistance to Trastuzumab In vivo Overexpress Epidermal Growth Factor Receptor and ErbB Ligands and Remain Dependent on the ErbB Receptor Network" *Clin. Canc. Res.* 13(16) (2007) pp. 4909-4919.
Roberts, et al. "Quantitative nuclease protection assay in paraffin-embedded tissue replicates prognostic microarray gene expression in diffuse large-B-cell lymphoma" *Labor. Invest.* 87 (2007) pp. 979-997.
Sawyers, C.L. "The cancer biomarker problem" *Nature* 452 (2008) pp. 548-552.
Sergina, et al. "Escape from HER family tyrosine kinase inhibitor therapy by the kinase inactive HER3" *Nature* 445 (2007) pp. 437-441.
Zhou, et al. "Targeting ADAM-mediated ligand cleavage to inhibit HER3 and EGFR pathways in non-small cell lung cancer" *Canc. Cell* 10 (2006) pp. 39-50.
Zweig, et al. "Receiver-Operating Characteristic (ROC) Plots: A Fundamental Evaluation Tool in Clinical Medicine" *Clin. Chem.* 39 (1993) pp. 561-577.
Huang, Abnormal expression of THBS1, SDC2 and CYR61 in esophageal squamous cell carcinoma and their prognostic significance, Dec. 15, 2011 (with translation), 7 total pages.

* cited by examiner

Heavy chain CDR amino acid alignments

| Antibody | CDR1 | | CDR2 | | CDR3 | |
|---|---|---|---|---|---|---|
| CAN017 | DY--AMS | (SEQ ID NO: 1) | TISDGGTYTYYPDSVKG | (SEQ ID NO: 2) | EWG--DYDGPDY | (SEQ ID NO: 3) |
| 04D01 | SH--WLH | (SEQ ID NO: 11) | VLDPSDFYSNYNQNFKG | (SEQ ID NO: 12) | GLL-SGDYAMDY | (SEQ ID NO: 13) |
| 09D03 | TFGLSVG | (SEQ ID NO: 21) | HIWWDDD-KYYNPALKS | (SEQ ID NO: 22) | IG--ADALPFDY | (SEQ ID NO: 23) |
| 11G01 | DH--IIH | (SEQ ID NO: 31) | YIYPRDGYIKYNEKFKG | (SEQ ID NO: 32) | G-----YYYAMDY | (SEQ ID NO: 33) |
| 12A07 | SY--WMH | (SEQ ID NO: 40) | MIDPSDVYTNYNPKFKG | (SEQ ID NO: 41) | ------NYSGDY | (SEQ ID NO: 42) |
| 18H02 | TY--GMS | (SEQ ID NO: 47) | NINTYSGVPTYADDFKG | (SEQ ID NO: 48) | GRDGYQVAWFAY | (SEQ ID NO: 49) |
| 22A02 | NY--WMH | (SEQ ID NO: 57) | MIDPSDSYTNYNPKFKG | (SEQ ID NO: 58) | ------NYSGDY | (SEQ ID NO: 42) |

FIG. 1

Complete heavy chain variable region amino acid alignments

| Antibody | | | CDR1 | CDR2 |
|---|---|---|---|---|
| CAN017 | (1) | QVQLVESGGGLVKPGGSLRLSCAASGFTFS | DY--AMS | WIRQAPGKGLEWVS TISDGGTYTYYPDSVKG RF |
| 04D01 | (1) | QVQLQQPGAELVRPGTSVKLSCKASGYTFT | SH--WLH | WVKQRPGQGLEWIG VLDPSDFYSNYNQNFKG KA |
| 09D03 | (1) | QVTLKESGPGILRPSQTLSLTCSFSGFSLS | TFGLSVG | WIRQPSGKGLEWLA HIWWDDD-KYYNPALKS RL |
| 11G01 | (1) | QVQLQQSDAELVKPGASVKISCKVSGYTFT | DH--IIH | WMKQRPEQGLEWIG YIYPRDGYIKYNEKFKG KA |
| 12A07 | (1) | QVQLLQPGAELVRPGTSVKLSCKTSGYTFS | SY--WMH | WVKQRPGQGLEWIG MIDPSDVYTNYNPKFKG KA |
| 18H02 | (1) | QIQLVQSGPELKKPGEAVKISCKSSGYTFT | TY--GMS | WVKQAPGRALKWMG NINTYSGVPTYADDFKG RF |
| 22A02 | (1) | QVQLQQPGAELVRPGTSVKLSCKASGYTFT | NY--WMH | WVKQRPGQGLEWIG MIDPSDSYTNYNPKFKG KA |

| Antibody | | | CDR3 | | |
|---|---|---|---|---|---|
| CAN017 | (69) | TISRDNAKNSLYLQMNSLRAEDTAVYYCAR | EWG--DYDGPDY | WGQGTLVTVSS | (SEQ ID NO: 7) |
| 04D01 | (69) | TLTVDTSSSTAYMQLSSLTSEDSAVYYCAR | GLL-SGDYAMDY | WGQGTSVTVSS | (SEQ ID NO: 17) |
| 09D03 | (70) | TISKDTSKNQVFLKIANVDTADTATYYCAR | IG--ADALPFDY | WGQGTTLTVSS | (SEQ ID NO: 27) |
| 11G01 | (69) | TLTADKSSSTAYMQVNSLTSEDSAVYFCAR | G-----YYYAMDY | WGQGTSVTVSS | (SEQ ID NO: 36) |
| 12A07 | (69) | TLTVDTSSSTAYMQLSSLTSEDSAVYYCAR | ------NYSGDY | WGQGTTLTVSS | (SEQ ID NO: 43) |
| 18H02 | (69) | AFSLESSASTAYLQINNLKNEDTATYFCAR | GRDGYQVAWFAY | WGQGTLVTVSA | (SEQ ID NO: 53) |
| 22A02 | (69) | TLTVDTSSSTAYMQLSSLTSEDSAVYYCAR | ------NYSGDY | WGQGTTLTVSS | (SEQ ID NO: 59) |

FIG. 2

Light (Kappa) chain CDR amino acid alignments

```
Antibody    CDR1                                  CDR2                          CDR3
CAN017      RASQEISG------YLS   (SEQ ID NO: 4)    AASTLDS (SEQ ID NO: 5)        LQYDSYPYT (SEQ ID NO: 6)
04D01       RSSQSIVHSNGNTYLE    (SEQ ID NO: 14)   KVSNRFS (SEQ ID NO: 15)       FQGSYVPWT (SEQ ID NO: 16)
09D03       RSSKSLLHSNGNTYLY    (SEQ ID NO: 24)   RMSNLAS (SEQ ID NO: 25)       MQHLEYPFT (SEQ ID NO: 26)
11G01       RSSQSIVHSIGNTYLE    (SEQ ID NO: 34)   KVSNRFS (SEQ ID NO: 15)       FQGSHVPFT (SEQ ID NO: 35)
12A07       RSSQSIVHSNGNTYLE    (SEQ ID NO: 14)   KVSNRFS (SEQ ID NO: 15)       FQGSYVPWT (SEQ ID NO: 16)
18H02       ITSTDIDDD------MN   (SEQ ID NO: 50)   EGNTLRP (SEQ ID NO: 51)       LQSDNLPYT (SEQ ID NO: 52)
22A02       RSSQSIVHSNGNTYLE    (SEQ ID NO: 14)   KVSNRFS (SEQ ID NO: 15)       FQGSYVPWT (SEQ ID NO: 16)
```

FIG. 3

Complete light (Kappa) chain variable region amino acid alignments

```
Antibody                                           CDR1                        CDR2
CAN017   (1)  DIQMTQSPSSLSASVGDRVTITC RASQEISG------YLS WYQQKPGKAPKRLIY AASTLDS GVPSRFSGS
04D01    (1)  DVLMTQIPLSLPVSLGDQASISC RSSQSIVHSNGNTYLE WYLQKPGQSPKSLIY KVSNRFS GVPDRFSGS
09D03    (1)  DIVLTQTAPSVPVTPGESVSISC RSSKSLLHSNGNTYLY WFLQRPGQSPQLLIY RMSNLAS GVPDRFSGS
11G01    (1)  DVLMTQTPLSLPVSLGDQASISC RSSQSIVHSIGNTYLE WYLQRPGQSPKLLIY KVSNRFS GVPERFSGS
12A07    (1)  DVLMTQIPLSLPVSLGDQASISC RSSQSIVHSNGNTYLE WYLQRPGQSPKLLIY KVSNRFS GVPDRFSGS
18H02    (1)  ETTVTQSPASLSMAIGDKVTIRC ITSTDIDDD------MN WYQQKPGEPPKLLIS EGNTLRP GVPSRFSGS
22A02    (1)  DVLMTQTPSLPVSLGDQASISC  RSSQSIVHSNGNTYLE WYLQKPGQSPKLLIY KVSNRFS GVPDRFSGS CDR3
CAN017   (66) GSGTEFTLTISSLQPEDFATYYC LQYDSYPYT FGQGTKLEIK   (SEQ ID NO: 8)
04D01    (71) GSGTDFTLKISRVEAEDLGVYYC FQGSYVPWT FGGGTKLEIK   (SEQ ID NO: 18)
09D03    (71) GSGTAFTLRISRVEARDVGVYYC MQHLEYPFT FGSGTKLEIK   (SEQ ID NO: 28)
11G01    (71) GSGTDFTLKISRVEAEDLGVYYC FQGSHVPFT FGSGTKLEIK   (SEQ ID NO: 37)
12A07    (71) GSGTDFTLKISRVEAEDLGVYYC FQGSYVPWT FGGGTKLEIK   (SEQ ID NO: 44)
18H02    (66) GYGTDFIFTIENMLSEDVADYYC LQSDNLPYT FGGGTKLEIK   (SEQ ID NO: 54)
22A02    (71) GSGTDFTLKISRVEAEDLGVYYC FQGSYVPWT FGGGTKLEIK   (SEQ ID NO: 60)
```

```
  1 mdrvpaqll qllllwlrga reqvqlvesg ggvlvkpggsl rlscaasgft fsdyamswir
 61 qapkglewv stisdggtyt yypdsvkgrf tisrdnakns lylqmnslra edtavyycar
121 ewgdydgfdy wgqgtlvtvs sastkgpsvf plapssksts ggtaalgclv kdyfpepvtv
181 swnsgaltsg vhtfpavlqs sglyslssvv tvpsslgtq tyicnvnhkp sntkvdkrve
241 pkscdkthtc ppcpapellg gpsvflfppk pkdtlmisrt pevtcvvvdv shedpevkfn
301 wyvdgvevhn aktkpreegy nstyrvvsvl tvlhqdwlng keyckcvsnk alpapiekti
361 skakgqprep qvytlppsre emtknqvslt clvkgfypsd iavewesngg pennykttpp
421 vldsdgsffl yskltvdksr wqqgnvfscs vmhealhnhy tqkslslspg k
(SEQ ID NO: 9)
```

(B)

```
  1 mdrvpaqll qllllwlrga rdiqmtqsp solsasvgdr vtitcrasqg isgylswyqq
 61 kpgkapkrli yaasstldsgv psrfsgsgsg teftltissl qpedfatyyc lqydsypytf
121 gqgtkleikr tvaapsvfif ppsdeqlksg tasvvcllnn fypreakvqw kvdnalqsgn
181 sqesvteqds kdstyslsst ltlskadyek hkvyacevth qglsspvtks fnrgec
(SEQ ID NO: 10)
```

```
  1 mgwscliivl vatatgvhsq vqlqqpgsel vrpgtsvkls ckaasgytfts hwlhwvkqrp
 61 gqglewigvl dpsdfysayn qnfkgkatlt vdtasstaym qlssltseds avyycargll
121 sqdyamdywg qgtsvtvssa kttppsvypl apgsaaqtns mvtlgclvkg yfpepvtvtw
181 nsgslssgvh tfpavlqsdl ytlssvtvp astwpsqtvt cnvahpasst kvdkkivprd
241 cgckpcictv pevssvflfp pkpkdvltit ltpkvtcvvv diskddpevq fswfvddvev
301 htaqtqpree qfnstfravs elpimhqdwl ngkefkcrvn saafpapiek tisktkgrpk
361 apqvytlppp keqmakdkvs ltcmitdffp editvewqwn gqpaenyknt qpimdtdgsy
421 fvysklnvqk snweagntft csvlheglhn hhteksIshs pgk
(SEQ ID NO: 19)
```

(B)

```
  1 mklpvrllvl mfwipassad vltqiplsl pvslgdqasi scrssqslvh sngntylewy
 61 lqkpgqspks liykvsnrfs qvpdrfsgsg sgtdftlkis rveaedlgvy ycfqgsypw
121 tfgggtklei kradaaptvs ifppsseqlt sggasvvcfl nnfyprdinv kwkidgserq
181 ngvlnswtdq dskdstyams stltltkdey erhnsytcea thktstspiv ksfnrned
(SEQ ID NO: 20)
```

```
  1  mgrltaafll livpayvlsq vtlkesgpgl lrpsqtlalt csfsqfslst fglsvgwirq
 61  pagkglewla hiwwdddkyy npalksrlti skdtsknqvf lklanvdtad tatyycarig
121  adalpfdywg qgttltvssa kttppsvypl apgcgdtcgs svtsgclvkg yfpepvtvtw
181  nsgslsasvh tfpallqsgl ytmsssvtvp sstwpsqtvt csvahpasst tvdkklepsg
241  pistinpcpp ckechkcpap nleggpsvfi fppnikdvlm isltpkvtcv vvdvsedcpd
301  vqiswfvnnv evhtaqtqth redynstirv vstlpiqhqd wmsgkefkck vnnkdlpapi
361  ertiskikgl vrapqvytlp ppaeqlsrkd valtclvvgf npgdisvewt snghteenyk
421  dtapvldsdg syfiysklnm ktskwektds facnvrhegl knyylkktis rspgk
(SEQ ID NO: 29)
```

(B)

```
  1  mrclseflgl lvlwipgalg divltqtaps vpvtpgesvs iscrsskell hsngntylyw
 61  flqrpgqspq lliyrmsnla sgvpdrfsgs qsgtaftlri srveasdvgv yycmqhlsyp
121  ftfgsgtkle ikradaaptv sifppsseql tsggasvvcf lnnfyprdin vkwkidgser
181  qngvlnswtd qdskdstysm sstltltkde yerhnsytce athktstspi vksfnrnec
(SEQ ID NO: 30)
```

```
  1  mewswvslff lsvttgvhsq vqlqqsdael vkpgasvkis ckvsgytftd hiihwmkqrp
 61  eqglewigyi yprdgyikyn ekfkgkatlt adkssstaym qvnsltseds avyfcargyy
121  yamdywgqgt svtvasaktt ppsvyplapg saaqtnsmvt lgclvkgyfp epvtvtwnsg
181  slsagvhtfp avlqsdlytl sssvtvpsst wpsqtvtcnv ahpasstkvd kkivprdcgc
241  kpcictvpev ssvfifppkp kdvltitltp kvtcvvvdis kdpevqfsw fvddvevhta
301  qtqpreeqfn stfrsvselp imhqdwlngk efkcrvnssa fpaplektis ktkgrpkapq
361  vytippkkeq makdkvsltc mitdffpedi tvewqwngqp aenyknstqpi mdtdgsyfvy
421  sklnvqksnw eagntftcsv lheglhnhht eksisshspgk
(SEQ ID NO: 38)
```

(B)

```
  1  mklpvrllvl mfwipasrsd vlmtqtplsl pvslgdqasi scrssqsivh signtylewy
 61  lqkpgqspkl liykvsnrfs qvperfsgsg sgtdftlkis rveaedlgvy ycfqgshvpf
121  tfgsgtklei kradaaptvs ifppsseqlt sggasvvcfl nnfypkdinv kwkidgserq
181  ngvlnswtdq dskdstysms stltltkdey erhnsytcea thktstspiv ksfnrnec
(SEQ ID NO: 39)
```

```
  1 mgwsclivll vstatcvhsq vqllqpgael vrpgtsvkis cktsgytfss ywmhwvkqrp
 61 gqglewigmi dpsdvytnyn pkfkgkatlt vdtsestsym qlssltsedS avyycarnys
121 gdywgqgttl tvsaakttpp svyplapgsa aqtnsmvtlg clvkgyfpep vtvtwnsgsl
181 ssqvhtfpav lqsdlytlss svtvpsstwp sqtvtcnvah passtkvdkk ivprdcqckp
241 cictvpevss vfifppkpkd vltitltpkv tcvvvdiskd dpevqfswfv ddvevhtaqt
301 qpreeqfnst fravaelpim hqdwlngkef korvnsaafp apiektiskt kgrpkspqvy
361 tipppkeqma kdkvsltcmi tdffpeditv ewqvngqpae nykntqpimd tdgsyfvysk
421 lnvqksnwea gntftcsvlh eglhnhhtek slshspgk
(SEQ ID NO: 45)
```

(B)

```
  1 mklpvrllvl mfwipassed vlmtqiplsl pvslgdqasi scrasqsivh sngntylewy
 61 lqkpgqspkl liykvsnrfs gvpdrfsgsg sgtdftlkis rveaedlgvy ycfqgsyvpw
121 tfgggtklei kradaaptvs ifppsseqlt sggasvvcfl nnfyprdinv kwkidgserq
181 ngvlnswtdq dskdstysms stltltkdey erhnsytcea thktstspiv ksfnrnec
(SEQ ID NO: 46)
```

```
  1 mgvlwnllfl msaaqsaqsq iqlvqsgpel kkpgsavkis cksagytftt ygnswvkqap
 61 grslkwmgwi ntysgvptya ddfkgrfafs lessastayl qinnlknedt styfcsrgrd
121 gyqvawfayw gqgtlvtvsa akttppsvyp lapgsaaqtn smvtlgclvk gyfpepvtvt
181 wnsgslssgv htfpavlqsd lytlsssvtv psstwpsqtv tcnvahpass tkvdkkivpr
241 dcqckpcict vpevssvfif ppkpkdvlti tltpkvtcvv vdiskddpev qfswfvddve
301 vhtaqtqpre eqfnstfrsv selpimhqdw lngkefkcrv nsaafpapie ktisktkgrp
361 kapqvytipp pkeqmakdkv sltcmitdff peditvewqv ngqpaenykn tqpimdtdgs
421 yfvysklnvq ksnweagntf tcsvlheglh nhhtekslsh spgk
(SEQ ID NO: 55)
```

(B)

```
  1 mfslalllsl llcvsdsra ettvtqspas lsmaigdkvt ircitstdid ddmnwfqqkp
 61 gappkllise qntlrpgvps rfsgsgygtd fiftiesmls edvadyyclq sdnlpytfgg
121 gtkleikrad aaptvsifpp sseqltsgga avvcflnnfy prdinvkwki dgserqngvl
181 nswtdqdskd stysmsstlt ltkdeyerhn sytcesthkt stspivksfn rnec
(SEQ ID NO: 56)
```

```
  1 mgwsciivll vstatgvhsq vqlqqpgael vrpgtsvkls ckasgytfts ywmhwvkqrp
 61 gqglewigmi dpsdsytnyn pkfkgkatlt vdtssstaym qlssltseds avyycarnys
121 gdywgqgttl tvssakttpp svplapqsa sqtnsmvtlg clvkgyfpep vtvtwnsgal
181 ssgvhtfpav lqsdlytlss svtvpsstwp sqtvtcnvah passtkvdkk ivprdcgckp
241 cictvpevss vflfppkpkd vltitltpkv tcvvvdiskd dpevqfswfv ddvevhtaqt
301 qpreeqfnst frsvselpim hqdwlngkef kcrvnsaafp apiektiskt kgrpkapqvy
361 tippkeqma kdkvsltcmi tdffpeditv ewqwngqpae nyknptqpimd tdgsyfvysk
421 lnvqksnwea gntftcsvlh eglhnhhtek slshspgk
(SEQ ID NO: 61)
```

(B)

```
  1 mklpvrllvl mfwipasssd vlmtqtplsl pvslgdqasi scrssqsivh sngntylewy
 61 lqkpgqspkl liykvsnrfs gvpdrfsgsg sgtdftlkis rveaedlgvy ycfqgsyvpw
121 tfgggtklei kradaaptvs ifppsseqlt sggasvvcfl nnfyprdinv kwkidgserq
181 ngvlnswtdq dskdstysms stltltkdey erhnsytcea thktstspiv ksfnrnec
(SEQ ID NO: 62)
```

FIG. 11

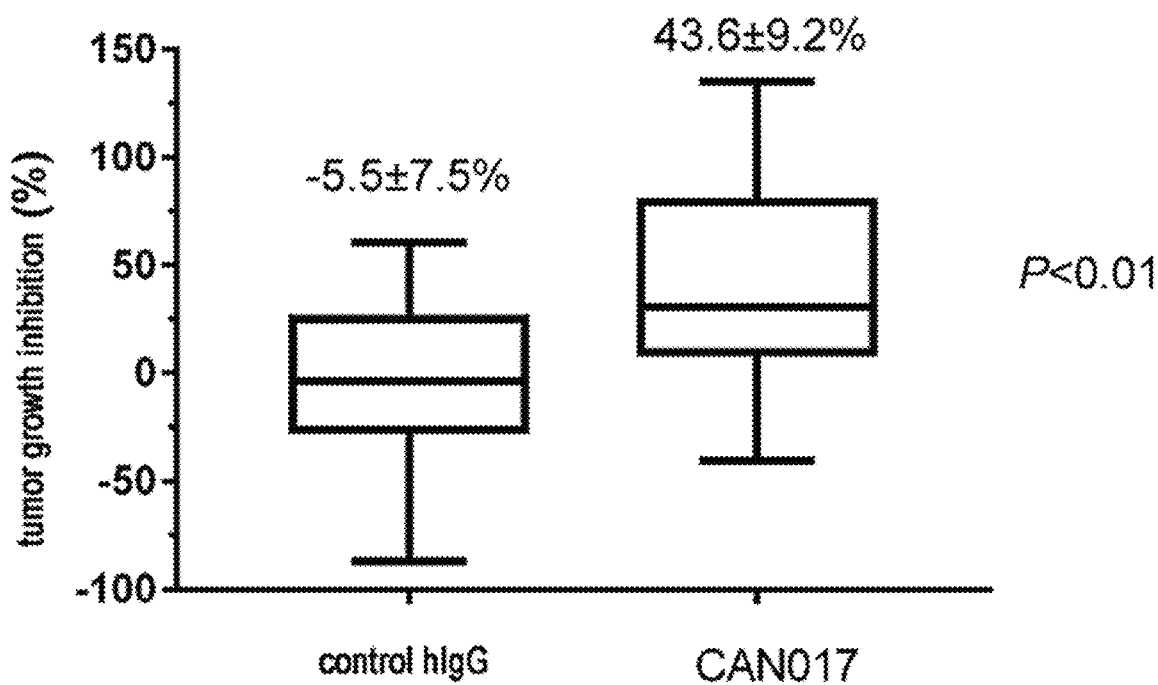

FIG. 12

METHOD FOR PREDICTING RESPONSE OF ESOPHAGUS CANCER TO ANTI-ERBB3 ANTIBODY THERAPY, AND KIT

CROSS REFERENCE TO RELATED APPLICATIONS

This application is the U.S. National Stage entry of International Application Number PCT/CN2018/090790, filed under the Patent Cooperation Treaty and having a filing date of Jun. 12, 2019, which claims priority to Chinese Patent Application 201710485107.3, having a filing date of Jun. 22, 2017, both of which are incorporated herein by reference in their entirety.

SEQUENCE LISTING

This application contains a Sequence Listing that has been submitted electronically in ASCII format and is hereby incorporated by reference in its entirety. Said ASCII copy, created on Mar. 29, 2020, is named KING-28-WO-US_Sequence_List.txt and is 68,180 bytes in size.

FIELD OF THE INVENTION

The field of the invention relates to clinical molecular diagnostics of tumors.

BACKGROUND

Most antitumor drugs are effective in some cancer patients, but not in others. This results from genetic variation among tumors, and can be observed even among different tumors within the same patient. Patient responses are more diverse with respect to targeted therapeutics. Therefore, the full potential of targeted therapies cannot be realized without suitable methods for predicting which patients will benefit from which drugs. According to the National Institutes of Health (NIH), the term "biomarker" is defined as "a characteristic that is objectively measured and evaluated as an indicator of normal biologic or pathogenic processes or pharmacological response to a therapeutic intervention" (Biomarkers Definitions Working Group, 2001, Clin. Pharmacol. Ther. 69:89-95).

Identifying, in advance, which patients most likely to show a clinical response to a given drug can accelerate new drug development. Meanwhile, this would significantly reduce the size, duration and cost of clinical trials. At present, technologies such as genomics, proteomics and molecular imaging currently enable rapid, sensitive and reliable detection of specific gene mutations, expression levels of particular genes, and other molecular biomarkers. In spite of various technologies for molecular characterization of tumors, the clinical utilization of cancer biomarkers remains largely unrealized because few cancer biomarkers are known. For example, a recent review article shows:

There is a critical need for expedited development of biomarkers and their use to improve diagnosis and treatment of cancer. (Cho, 2007, Molecular Cancer 6:25).

Another recent review article on cancer biomarkers indicates: Now the challenge is to discover cancer biomarkers. Although molecularly targeted agents have been successfully used clinically in many types of tumors, such as chronic myeloid leukemia, gastrointestinal stromal tumor, lung cancer and glioblastoma multiforme, the ability to apply such successes in a broader context is severely limited by the lack of an efficient strategy to evaluate patients' response to the targeted agents. The problem mainly lies in the inability to select patients with molecularly defined cancers for clinical trials to evaluate these new drugs. Thus biomarkers that reliably identify those patients who are most likely to benefit from a particular agent are required (Sawyers, 2008, Nature 452:548-552, at 548).

Documents such as the foregoing illustrate the need for the discovery of clinically useful biomarkers and diagnostic methods based on such biomarkers.

There are three distinct types of cancer biomarkers: (1) prognostic biomarkers, (2) predictive biomarkers, and (3) pharmacodynamic (PD) biomarkers. A prognostic biomarker is used to classify a cancer, e.g., a solid tumor, according to aggressiveness, i.e., rate of growth and/or metastasis, and refractiveness to treatment. This is sometimes called distinguishing "good outcome" tumors from "poor outcome" tumors. A predictive biomarker is used to assess the probability that a particular patient will benefit from treatment with a particular drug. For example, patients with breast cancer in which the ERBB2 (HER2) gene is amplified are likely to benefit from treatment with trastuzumab (HERCEPTIN®), whereas patients without ERBB2 gene amplification are unlikely to benefit from treatment with trastuzumab. A PD biomarker is an indication of the effect(s) of a drug on its molecular target while the patient is taking the drug. Accordingly, PD biomarkers often are used to show dosage level and dosing frequency, during the early stages of clinical development of a new drug. For a discussion of cancer biomarkers, see Sawyers, 2008, Nature 452:548-552.

Tumors driven by EGFR or HER2 often respond to treatment with inhibitors of EGFR or HER2, but these tumors invariably develop resistance to these inhibitors. At least one mechanism of acquired resistance to anti-EGFR or anti-HER2 treatment is activation of ERBB3 (also known as HER3) signaling. See, e.g., Engelman et al, 2006, Clin. Cancer Res. 12:4372; Ritter et al, 2007, Clin. Cancer Res. 13:4909; Sergina et al, 2007, Nature 445:437. NRG1-induced activation of HER2-ERBB3 heterodimers also has been associated with resistance to EGFR inhibitors (Zhou et al, 2006, Cancer Cell 10:39). Thus, ERBB3 plays an important role in development of drug resistance, as well as being involved in tumor initiation and maintenance, through its heterodimerization with EGFR and HER2. Consequently, there has been interest in development of ERBB3 inhibitors, especially anti-ERBB3 antibodies, since ERBB3 lacks kinase activity.

As with other types of targeted therapy, some, but not all, tumors respond to anti-ERBB3 therapy. Therefore, there is a need for diagnostic methods based on predictive biomarkers that can be used to identify patients with tumors that are likely (or unlikely) to respond to treatment with an ERBB3 inhibitor such as an anti-ERBB3 antibody.

Recently, it is discovered that neuregulin-1 (NRG1) expression in a tissue sample from a mammalian tumor (e.g., a human tumor) correlates with sensitivity of the tumor to treatment with an ERBB3 inhibitor, e.g., an anti-ERBB3 antibody. As a major ligand of ERBB3, NRG1 can promote heterodimerization of ERBB3 and other ERBB family members, thereby activating a variety of intracellular signaling pathways. Meetze et al. reported that tumor growth inhibition (TGI) caused by anti-ERBB3 antibodies was not related to the expression level of ERBB3, but was significantly related to the expression level of NRG1, that is, when the expression level of NRG1 in tumor samples was equal to or higher than a certain threshold, the tumor may respond to treatment with an anti-ERBB3 antibody. Therefore, NRG1 is expected to be an effective biomarker for predicting whether tumors will respond to treatment with an ERBB3 inhibitor such as an anti-ERBB3 antibody (see CN103959065A and Sergina et al., 2015, Clin Cancer Res; 21(5), 1106-1113).

However, the inventors have found that in xenograft models of esophageal cancer, although models with low NRG1 expression levels are always insensitive to an anti-ERBB3 antibody, models with high NRG1 expression levels may respond or not to treatment with anti-ERBB3 antibody (see Example 2), indicating that the method of using NRG1 alone as a biomarker to predict whether esophageal cancer will respond to treatment with an anti-ERBB3 antibody is not very effective.

Therefore, other biomarkers need to be provided that, when used alone or in combination with NRG1, can accurately predict whether esophageal cancer will respond to treatment with anti-ERBB3 antibodies.

SUMMARY OF INVENTION

The invention is based, in part, on the discovery that the expression levels of SDC2, PTGES, NCF2, NOXA1, CARD6, and GNAZ in a tissue sample obtained from an esophageal cancer correlate with sensitivity of esophageal cancer to treatment with an anti-ERBB3 antibody. Surprisingly, the inventor has discovered that the correlation is strong enough that the expression level alone of each of the six biomarkers SDC2, PTGES, NCF2, NOXA1, CARD6, and GNAZ is sufficient to predict whether esophageal cancer is sensitive or resistant to treatment with an anti-ERBB3 antibody. The inventors have further discovered that the combined use of the above-mentioned biomarkers (i.e., using two or more biomarkers) will further increase the effectiveness of predicting the sensitivity of esophageal cancer to treatment with anti-ERBB3 antibodies. Accordingly, the invention provides a method for predicting whether esophageal cancer is sensitive or resistant to treatment with an ERBB3 inhibitor (e.g., an anti-ERBB3 antibody). The method includes: (a) measuring expression levels of one or more biomarkers selected from SDC2, PTGES, NCF2, NOXA1, CARD6 and GNAZ in an esophageal cancer sample; and (b) comparing the expression levels with a threshold expression level of a corresponding biomarker, wherein an expression level of the SDC2 and/or GNAZ that is equal to or lower than the threshold expression level, and/or an expression level of one or more biomarkers selected from PTGES, NCF2, NOXA1 or CARD6 that is equal to or higher than the threshold expression level indicate that the esophageal cancer is sensitive to treatment with an ERBB3 inhibitor (e.g., an anti-ERBB3 antibody). On the contrary, wherein an expression level of the SDC2 and/or GNAZ that is higher than the threshold expression level, and/or an expression level of one or more biomarkers selected from PTGES, NCF2, NOXA1 or CARD6 that is lower than the threshold expression level indicate that the esophageal cancer is resistant to treatment with an ERBB3 inhibitor (e.g., an anti-ERBB3 antibody).

In one embodiment, the method of the present invention further comprises measuring the expression level of the NRG1 gene, wherein an expression level of NRG1 that is equal to or higher than the threshold expression level indicates that the esophageal cancer is sensitive to treatment with an ERBB3 inhibitor (e.g., an anti-ERBB3 antibody).

In one embodiment, the method of the present invention includes: (a) measuring expression levels of one or more biomarkers selected from SDC2, PTGES, NCF2, NOXA1, CARD6 and GNAZ in an esophageal cancer sample; and (b) comparing the expression levels with a threshold expression level of a corresponding biomarker, wherein an expression level of the SDC2 and/or GNAZ that is equal to or lower than the threshold expression level, and an expression level of one or more biomarkers selected from PTGES, NCF2, NOXA1 or CARD6 that is equal to or higher than the threshold expression level indicate that the esophageal cancer is sensitive to treatment with an ERBB3 inhibitor (e.g., an anti-ERBB3 antibody).

The expression levels of the biomarkers of the present invention (i.e., SDC2, PTGES, NCF2, NOXA1, CARD6, GNAZ, and NRG1) refer to the expression level of a protein or the expression level of an mRNA. The expression of the protein can be measured by various methods well known to those skilled in the art, such as immunohistochemistry (IHC) analysis, enzyme-linked immunosorbent assay (ELISA), western blotting, immunofluorescence, and the like. The expression level of the mRNA can also be measured by various methods well known to those skilled in the art, such as fluorescent quantitative PCR, microarray, digital PCR, transcriptome sequencing technology (RNAseq), and the like.

Another aspect of the invention provides a use of an agent that measures the expression level of one or more biomarkers selected from the group consisting of SDC2, PTGES, NCF2, NOXA1, CARD6, and GNAZ in esophageal cancer samples in the preparation of a diagnostic test kit for identifying whether esophageal cancer is sensitive or resistant to treatment with an anti-ERBB3 antibody. In one embodiment, the above-mentioned biomarkers further include NRG1.

Another aspect of the invention provides a diagnostic test kit for predicting whether esophageal cancer is sensitive or resistant to treatment with an anti-ERBB3 antibody, wherein the kit comprises an agent that measures the expression level of one or more biomarkers selected from SDC2, PTGES, NCF2, NOXA1, CARD6, and GNAZ in esophageal cancer samples. In one embodiment, the kit of the present invention also includes a reagent for measuring the expression level of NRG1. The reagents are reagents known to those skilled in the art for measuring the expression level of mRNAs or a protein of a gene. For example, when the mRNA expression level is measured by a fluorescent real-time quantitative PCR, the reagent includes a primer for specifically amplifying the biomarker of the present invention, a DNA polymerase, and a buffer, a reactant, and the like for measuring its expression level. When the protein expression level is measured by an IHC analysis, the reagent includes an antibody (primary antibody) against the biomarker of the present invention, and a detection antibody (secondary antibody) that binds to the primary antibody, and the like. In one embodiment, the kit of the invention further comprises a reagent for measuring the expression level of one or more other genes used as a control.

BRIEF DESCRIPTION OF THE DRAWINGS

FIG. 1 is a schematic diagram showing the CDRHi, CDRH2, and CDRH3 sequences (Kabat definition) of the immunoglobulin heavy chain variable regions sequences for the anti-ERBB3 antibodies denoted as CAN017, 04D01, 09D03, 1 1G01, 12A07, 18H02 and 22A02 (which correspond to the regions shown in the boxes in FIG. 2).

FIG. 2 is a schematic diagram showing the amino acid sequence of the complete immunoglobulin heavy chain variable region for the anti-ERBB3 antibodies denoted as CAN017, 04D01, 09D03, 11G01, 12A07, 18H02 and 22A02. The amino acid sequences for each antibody are aligned against one another, and Complementary Determining Sequences (CDR) (Kabat definition), $CDR_{H1}$, $CDR_{H2}$, and $CDR_{H3}$, are identified in boxes. The sequences outside the boxes represent framework (FR) sequences.

FIG. 3 is a schematic diagram showing the $CDR_{L1}$, $CDR_{L2}$, and $CDR_{L3}$ sequences (Kabat definition) of the immunoglobulin light chain variable regions sequences for the anti-ERBB3 antibodies denoted as CAN017, 04D01, 09D03, 11G01, 12A07, 18H02 and 22A02 (which correspond to the regions shown in the boxes in FIG. 4).

FIG. 4 is a schematic diagram showing the amino acid sequence of the complete immunoglobulin light chain variable region for the anti-ERBB3 antibodies denoted as CAN017, 04D01, 09D03, 11G01, 12A07, 18H02 and 22A02. The amino acid sequences for each antibody are aligned against one another, and Complementary Determining Sequences (CDR) (Kabat definition), $CDR_{L1}$, $CDR_{L2}$, and $CDR_{L3}$, are identified in boxes. The sequences outside the boxes represent framework (FR) sequences.

FIG. 5 provides the amino acid sequence defining the (A) full length CAN017 immunoj globulin heavy chain and (B) the full length CAN017 immunoglobulin light chain.

FIG. 6 provides the amino acid sequence defining the (A) full length 04D01 immunoj globulin heavy chain and (B) the full length 04D01 immunoglobulin light chain.

FIG. 7 provides the amino acid sequence defining the (A) full length 09D03 immunoj globulin heavy chain and (B) the full length 09D03 immunoglobulin light chain.

FIG. 8 provides the amino acid sequence defining the (A) full length 11G01 immunoj globulin heavy chain and (B) the full length 11 GO 1 immunoglobulin light chain.

FIG. 9 provides the amino acid sequence defining the (A) full length 12A07 immunoj globulin heavy chain and (B) the full length 12A07 immunoglobulin light chain.

FIG. 10 provides the amino acid sequence defining the (A) full length 18H02 immunoj globulin heavy chain and (B) the full length 18H02 immunoglobulin light chain.

FIG. 11 provides the amino acid sequence defining the (A) full length 22A02 immunoj globulin heavy chain and (B) the full length 22A02 immunoglobulin light chain.

FIG. 12 summarizes the results of experiments measuring the tumor suppressive activity of hIgG (20 mg/kg) and anti-ERBB3 antibody CAN017 (20 mg/kg) in a xenograft model of an esophageal cancer.

FIG. 13 (lower panel) is a significant analysis of the correlation between mRNA expression levels of SDC2 and tumor growth inhibition.

FIG. 14 (lower panel) is a significant analysis of the correlation between mRNA expression levels of GNAZ and tumor growth inhibition.

FIG. 15 (lower panel) is a significant analysis of the correlation between mRNA expression levels of NCF2 and tumor growth inhibition.

FIG. 16 (lower panel) is a significant analysis of the correlation between mRNA expression levels of NOXA1 and tumor growth inhibition.

FIG. 17 (lower panel) is a significant analysis of the correlation between mRNA expression levels of PTGES and tumor growth inhibition.

FIG. 18 (lower panel) is a significant analysis of the correlation between mRNA expression levels of CARD6 and tumor growth inhibition.

DETAILED DESCRIPTION OF THE INVENTION

Definitions

Figure 13:
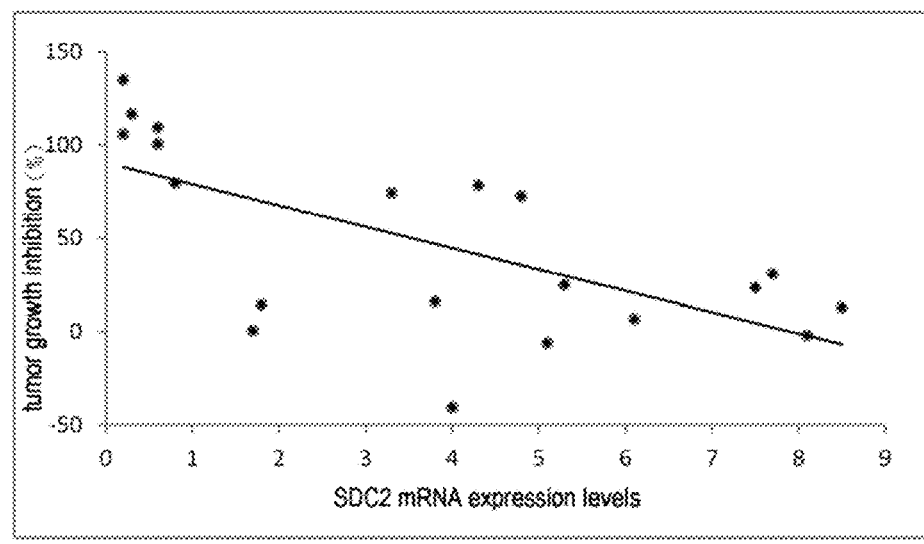
FIG. 13 (upper panel) is a scatter plot with a linear regression trend line showing the relationship between the in vivo efficacy of CAN017 in 20 xenograft models (expressed as percentage of tumor growth inhibition (TGI)) and mRNA expression levels of SDC2. The 20 data points are represented by (●), wherein the solid line indicates the correlation between the mRNA expression levels of SDC2 and tumor growth inhibition.

As used herein, "CAN017" means the humanized anti-human ERBB3 monoclonal antibody whose full-length heavy chain amino acid sequence is SEQ ID NO: 9, and whose full-length light chain amino acid sequence is SEQ ID NO: 10.

As used herein, "ERBB3" (also known as HER3) means the human protein encoded by the gene identified by Entrez Gene ID No. 2065, and allelic variants thereof.

As used herein, "ERBB3 inhibitor" means a molecule (small molecule or macromolecule, e.g., an antibody or antigen binding fragment thereof) that binds to ERBB3 and inhibits, neutralizes, prevents or eliminates the biological activity of ERBB3 in a tumor cell.

As used herein, "NRG1" (also known as neuregulin-1, heregulin, HRG and HRG1) means the human protein encoded by Entrez Gene ID No. 3084, and allelic variants thereof.

As used herein, "SDC2" (also known as multiligand proteoglycan 2) means the human protein encoded by Entrez Gene ID No. 6383, and allelic variants thereof.

As used herein, "NCF2" (also known as neutrophil cytoplasmic factor 2) means the human protein encoded by Entrez Gene ID No. 4688, and allelic variants thereof.

As used herein, "NOXA1" (also known as NADPH oxidase activator 1) means the human protein encoded by Entrez Gene ID No. 10811, and allelic variants thereof.

As used herein, "GNAZ" (also known as G protein subunit a Z) means the human protein encoded by Entrez Gene ID No. 2781, and allelic variants thereof.

As used herein, "PTGES" (also known as prostaglandin E synthase) means the human protein encoded by Entrez Gene ID No. 9536, and allelic variants thereof.

As used herein, "CARD6" (also known as caspase recruitment domain family member 6) means the human protein encoded by Entrez Gene ID No. 84674, and allelic variants thereof.

As used herein, "response" or "responding" to treatment means, with regard to a treated tumor, that the tumor displays: (a) slowing of growth, (b) cessation of growth, or (c) regression.

As used herein, "expression level" refers to the expression level of a biomarker of the invention in an esophageal cancer sample. For example, an expression level can be expressed as (1) mRNA expression level measured by RNAseq (standardized with FPKM), or (2) staining intensity in an IHC assay. The expression level of a biomarker of the invention can be interpreted with respect to a threshold expression level, which can be empirically determined in a threshold determination analysis, e.g., using ROC curve analysis.

As used herein, "threshold determination analysis" means analysis of a dataset of esophageal cancer, to determine a threshold expression level of the biomarker in esophageal cancer samples.

As used herein, "threshold expression level" means an expression level equal to or higher than which (for NRG1, NCF2, NOXA1, PTGES and CARD6) or equal to or lower than which (for SDC2 and GNAZ) an esophageal cancer is classified as being sensitive to treatment with an ERBB3 inhibitor.

ERBB3 Antibodies

The methods disclosed herein can be used for predicting esophageal cancer response to treatment with an ERBB3 inhibitor such as an anti-ERBB3 antibody, or antigen-binding fragment of an anti-ERBB3 antibody. In some embodiments, an esophageal cancer is classified as sensitive or resistant to an ERBB3 antibody (or antigen binding fragment thereof) that inhibits or prevents NRG1 (e.g., NRG1-β1) from binding to ERBB3, thereby indirectly inhibiting or preventing ligand-induced dimerization of ERBB3 (e.g., anti-ERBB3 antibodies CAN017, 04D01, 12A07, 18H02 and 22A02). In other embodiments, an esophageal cancer is classified as sensitive or resistant to an antibody (or antigen-binding fragment thereof) that inhibits or prevents ERBB3 dimerization, without preventing NRG1 binding to ERBB3 (e.g., anti-ERBB3 antibody 09D03 and 11GO1).

In exemplary embodiments, the ERBB3 inhibitor is one of the following antibodies: CAN017, 04D01, 12A07, 18H02, 22A02, 11G01, and 09D03.

Anti-ERBB3 antibody CAN017 comprises an immunoglobulin heavy chain variable region comprising a $CDR_{H1}$ comprising an amino acid sequence selected from the group consisting of SEQ ID NO: 1, a $CDR_{H2}$ comprising the amino acid sequence of SEQ ID NO: 2, and a $CDR_{H3}$ comprising the amino acid sequence of SEQ ID NO: 3 as shown in FIG. 1; and an immunoglobulin light chain variable region comprising a $CDR_{L1}$ comprising the amino acid sequence of SEQ ID NO: 4, a $CDR_{L2}$ comprising the amino acid sequence of SEQ ID NO: 5, and a $CDR_{L3}$ comprising the amino acid sequence of SEQ ID NO: 6 as shown in FIG. 3. In an exemplary embodiment, antibody CAN017 comprises an immunoglobulin heavy chain variable region comprising the amino acid sequence of SEQ ID NO: 7 as shown in FIG. 2, and an immunoglobulin light chain variable region comprising the amino acid sequence of SEQ ID NO: 8 as shown in FIG. 4. In another exemplary embodiment, antibody CAN017 comprises an immunoglobulin heavy chain amino acid sequence of SEQ ID NO: 9 and an immunoglobulin light chain amino acid sequence of SEQ ID NO: 10, as shown in FIG. 5.

Anti-ERBB3 antibody 04D01 comprises an immunoglobulin heavy chain variable region comprising a $CDR_{H1}$ comprising the amino acid sequence of SEQ ID NO: 11, a $CDR_{H2}$ comprising the amino acid sequence of SEQ ID NO: 12, and a $CDR_{H3}$ comprising the amino acid sequence of SEQ ID NO: 13 as shown in FIG. 1; and an immunoglobulin light chain variable region comprising a $CDR_{L1}$ comprising the amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16 as shown in FIG. 3. In an exemplary embodiment, antibody 04D01 comprises an immunoglobulin heavy chain variable region comprising the amino acid sequence of SEQ ID NO: 17 as shown in FIG. 2, and an immunoglobulin light chain variable region comprising the amino acid sequence of SEQ ID NO: 18 as shown in FIG. 4. In another exemplary embodiment, antibody 04D01 comprises an immunoglobulin heavy chain amino acid sequence of SEQ ID NO: 19 and an immunoglobulin light chain amino acid sequence of SEQ ID NO: 20, as shown in FIG. 6.

Anti-ERBB3 antibody 09D03 comprises an immunoglobulin heavy chain variable region comprising a $CDR_{H1}$ comprising the amino acid sequence of SEQ ID NO: 21, a $CDR_{H2}$ comprising the amino acid sequence of SEQ ID NO: 22, and a $CDR_{H3}$ comprising the amino acid sequence of SEQ ID NO: 23 as shown in FIG. 1; and an immunoglobulin light chain variable region comprising a $CDR_{L1}$ comprising the amino acid sequence of SEQ ID NO: 24, a $CDR_{L2}$ comprising the amino acid sequence of SEQ ID NO: 25, and a $CDR_{L3}$ comprising the amino acid sequence of SEQ ID NO: 26 as shown in FIG. 3. In an exemplary embodiment, antibody 09D03 comprises an immunoglobulin heavy chain variable region comprising the amino acid sequence of SEQ ID NO: 27 as shown in FIG. 2, and immunoglobulin light chain variable region comprising the amino acid sequence of SEQ ID NO: 28 as shown in FIG. 4. In another exemplary embodiment, antibody 09D03 comprises an immunoglobulin heavy chain amino acid sequence of SEQ ID NO: 29 and an immunoglobulin light chain amino acid sequence of SEQ ID NO: 30, as shown in FIG. 7.

Anti-ERBB3 antibody 11G01 comprises an immunoglobulin heavy chain variable region comprising a $CDR_{H1}$ comprising the amino acid sequence of SEQ ID NO: 31, a $CDR_{H2}$ comprising the amino acid sequence of SEQ ID NO: 32, and a $CDR_{H3}$ comprising the amino acid sequence of SEQ ID NO: 33 as shown in FIG. 1; and an immunoglobulin light chain variable region comprising a $CDR_{L1}$ comprising the amino acid sequence of SEQ ID NO: 34, a $CDR_{L2}$ comprising the amino acid sequence of SEQ ID NO: 15, and a $CDR_{L3}$ comprising the amino acid sequence of SEQ ID NO: 35 as shown in FIG. 3. In an exemplary embodiment, antibody 11G01 comprises an immunoglobulin heavy chain variable region comprising the amino acid sequence of SEQ ID NO: 36 as shown in FIG. 2, and an immunoglobulin light chain variable region comprising the amino acid sequence of SEQ ID NO: 37 as shown in FIG. 4. In another exemplary embodiment, antibody 11G01 comprises an immunoglobulin heavy chain amino acid sequence of SEQ ID NO: 38 and an immunoglobulin light chain amino acid sequence of SEQ ID NO: 39, as shown in FIG. 8.

Anti-ERBB3 antibody 12A07 comprises an immunoglobulin heavy chain variable region comprising a $CDR_{H1}$ comprising the amino acid sequence of SEQ ID NO: 40, a $CDR_{H2}$ comprising the amino acid sequence of SEQ ID NO: 41, and a $CDR_{H3}$ comprising the amino acid sequence of SEQ ID NO: 42 as shown in FIG. 1; and an immunoglobulin light chain variable region comprising a $CDR_{L1}$ comprising the amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16 as shown in FIG. 3. In an exemplary embodiment, antibody 12A07 comprises an immunoglobulin heavy chain variable region comprising the amino acid sequence of SEQ ID NO: 43 as shown in FIG. 2, and an immunoglobulin light chain variable region comprising the amino acid sequence of SEQ ID NO: 44 as shown in FIG. 4. In another exemplary embodiment, antibody 12A07 comprises an immunoglobulin heavy chain amino acid sequence of SEQ ID NO: 45 and an immunoglobulin light chain amino acid sequence of SEQ ID NO: 46, as shown in FIG. 9.

Anti-ERBB3 antibody 18H02 comprises an immunoglobulin heavy chain variable region comprising a $CDR_{H1}$ comprising the amino acid sequence of SEQ ID NO: 47, a $CDR_{H2}$ comprising the amino acid sequence of SEQ ID NO: 48, and a $CDR_{H3}$ comprising the amino acid sequence of SEQ ID NO: 49 as shown in FIG. 1; and an immunoglobulin light chain variable region comprising a $CDR_{L1}$ comprising the amino acid sequence of SEQ ID NO: 50, a $CDR_{L2}$ comprising the amino acid sequence of SEQ ID NO: 51, and a $CDR_{L3}$ comprising the amino acid sequence of SEQ ID NO: 52 as shown in FIG. 3. In an exemplary embodiment, antibody 18H02 comprises an immunoglobulin heavy chain variable region comprising the amino acid sequence of SEQ ID NO: 53 as shown in FIG. 2, and an immunoglobulin light chain variable region comprising the amino acid sequence of SEQ ID NO: 54 as shown in FIG. 4. In another exemplary embodiment, antibody 18H02 comprises an immunoglobulin heavy chain amino acid sequence of SEQ ID NO: 55 and an immunoglobulin light chain amino acid sequence of SEQ ID NO: 56, as shown in FIG. 10.

Anti-ERBB3 antibody 22A02 comprises an immunoglobulin heavy chain variable region comprising a $CDR_{H1}$ comprising the amino acid sequence of SEQ ID NO: 57, a $CDR_{H2}$ comprising the amino acid sequence of SEQ ID NO: 58, and a $CDR_{H3}$ comprising the amino acid sequence of SEQ ID NO: 42 as shown in FIG. 1; and an immunoglobulin light chain variable region comprising a $CDR_{L1}$ comprising the amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16 as shown in FIG. 3. In an exemplary embodiment, antibody 22A02 comprises an immunoglobulin heavy chain variable region comprising the amino acid sequence of SEQ ID NO: 59 as shown in FIG. 2, and an immunoglobulin light chain variable region comprising the amino acid sequence of SEQ ID NO: 60 as shown in FIG. 4. In another exemplary embodiment, antibody 22A02 comprises an immunoglobulin heavy chain amino acid sequence of SEQ ID NO: 61 and an immunoglobulin light chain amino acid sequence of SEQ ID NO: 62, as shown in FIG. 11.

It is contemplated that the skilled person would understand that a complete heavy or kappa chain antibody sequences can be created by ligating a variable region as described above to a respective constant region sequence(s) to produce active full length immunoglobulin heavy and light chains. For example, a complete heavy chain comprises a heavy variable sequence followed by the murine or human IgGI or IgG2b heavy chain constant sequence (which are known in the art) and a complete kappa chain comprises a kappa variable sequence followed by the murine or human kappa light chain constant sequence (which are known in the art). It is further contemplated that CDRI, CDR2, and CDR3 sequences from the immunoglobulin heavy and light chains may be interposed between human or humanized immunoglobulin framework regions.

Sample

A tissue sample from an esophageal cancer (e.g., a tissue sample from a human esophageal cancer obtained from a human patient, e.g., a human patient being considered for treatment with an ERBB3 inhibitor) can be used as a source of RNA, a source of protein, or a source of thin sections for immunohistochemistry (IHC), so the level of biomarkers of the invention in the sample can be determined in practicing the disclosed methods. The tissue sample can be obtained by using conventional tumor biopsy instruments and procedures. Endoscopic biopsy, excisional biopsy, incisional biopsy, fine needle biopsy, punch biopsy, shave biopsy and skin biopsy are examples of recognized medical procedures that can be used by one of skill in the art to obtain tumor samples. The tumor tissue sample should be large enough to provide sufficient RNA, protein, or thin sections for measuring gene expression of the biomarkers.

The tumor tissue sample can be in any form that allows measurement of expression or content of the biomarkers. In other words, the tissue sample must be sufficient for RNA extraction, protein extraction, or preparation of thin sections. Accordingly, the tissue sample can be fresh, preserved through suitable cryogenic techniques, or preserved through non-cryogenic techniques. A standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation for subsequent analysis are well-known to those of skill in the art.

Biomarker Expression

As described herein, determining or measuring the level of biomarkers expression in a tissue sample from a tumor can be performed by any suitable method. Several such methods are known in the art. For example, determining the expression level of the biomarkers can be done by measuring the level or amount of biomarkers protein, or measuring the level or amount of RNA of biomarkers, in a sample.

In some embodiments, classification of esophageal cancer as sensitive or resistant to treatment with an ERBB3 inhibitor is based solely on the expression of biomarkers in a tissue sample from the esophageal cancer. In other embodiments, expression of one or more other genes is measured in addition to the expression of the biomarkers of the invention, to classify a tumor as sensitive or resistant to treatment with an ERBB3 inhibitor. It is contemplated herein that in embodiments when the expression of one or more other genes is measured in addition to the biomarkers of the invention, the one or more other genes do not include ErbBI, ErbB2, and ErbB3 (e.g., monomers, heterodimers and/or homodimers of any of ErbBI, ErbB2 and ErbB3, and/or phosphorylated ErbBI, ErbB2 and ErbB3 either in monomeric or dimeric form). It is further contemplated herein that the expression of one or more other genes measured in addition to the biomarkers of the invention may include genes serving as controls or standards, e.g., for data normalization.

RNA Analysis

Methods for determining the expression level of the biomarkers of the invention at the mRNA level include, but not limited to, conventional microarray analysis, digital PCR, RNAseq and quantitative polymerase chain reaction (PCR). In some embodiments, RNA is extracted from the cells, tumor or tissue of interest using standard protocols. In other embodiments, RNA analysis is performed using techniques that do not require RNA isolation.

Methods for rapid and efficient extraction of eukaryotic mRNA from tissue samples are well known to those of skill in the art. See, e.g., Ausubel et al, 1997, Current Protocols of Molecular Biology, John Wiley & Sons. The tissue sample can be fresh, frozen or fixed paraffin-embedded (FFPE) samples such as clinical study esophageal cancer patient specimens. In general, RNA isolated from fresh or frozen tissue samples tends to be less fragmented than RNA from FFPE samples. FFPE samples of tumor material, however, are more readily available, and FFPE samples are suitable sources of RNA for use in methods of the present invention. For a discussion of FFPE samples as sources of RNA for gene expression profiling by RT-PCR, see, e.g., Clark-Langone et al, 2001, BMC Genomics 8:279. Also see, De Andres et al, 1995, Biotechniques 18:42044; and Baker et al, U.S. Patent Application Publication No. 2005/0095634. The commercially available kits with vendor's instructions for RNA extraction and preparation can be used. Commercial vendors of various RNA isolation products and complete kits include Qiagen (Valencia, CA), Invitrogen (Carlsbad, CA), Ambion (Austin, TX) and Exiqon (Woburn, MA).

In general, RNA isolation begins with tissue/cell disruption. During tissue/cell disruption it is desirable to minimize RNA degradation by RNases. One approach to limiting RNase activity during the RNA isolation process is to ensure that a denaturant is in contact with cellular contents as soon as the cells are disrupted. Another common practice is to include one or more proteases in the RNA isolation process. Optionally, fresh tissue samples are immersed in an RNA stabilization solution, at room temperature, as soon as they are collected. The stabilization solution rapidly permeates the cells, stabilizing the RNA for storage at 4° C., for subsequent isolation. One such stabilization solution is available commercially as RNAlater® (Ambion, Austin, TX).

In some protocols, total RNA is isolated from disrupted tumor material by cesium chloride density gradient centrifugation. In general, mRNA makes up approximately 1% to 5% of total cellular RNA. Immobilized Oligo(dT), e.g., oligo(dT) cellulose, is commonly used to separate mRNA from ribosomal RNA and transfer RNA. If stored after isolation, RNA must be stored under RNase-free conditions. Methods for stable storage of isolated RNA are known in the art. Various commercial products for stable storage of RNA are available.

Microarray

The mRNA expression level of the biomarkers can be measured using conventional DNA microarray expression profiling technology. A DNA microarray is a collection of specific DNA segments or probes affixed to a solid surface or substrate such as glass, plastic or silicon, with each specific DNA segment occupying a known location in the array. Hybridization with a sample of labeled RNA, usually under stringent hybridization conditions, allows detection and quantitation of RNA molecules corresponding to each probe in the array. After stringent washing to remove non-specifically bound sample material, the microarray is scanned by confocal laser microscopy or other suitable detection method. Modern commercial DNA microarrays, often known as DNA chips, typically contain tens of thousands of probes, and thus can measure expression of tens of thousands of genes simultaneously. Such microarrays can be used in practicing the present invention. Alternatively, custom chips containing as few probes as those needed to measure NRG1, plus necessary controls or standards, e.g., for data normalization, can be used in practicing the disclosed methods.

To facilitate data normalization, a two-color microarray reader can be used. In a two-color (two-channel) system, samples are labeled with a first fluorophore that emits at a first wavelength, while an RNA or cDNA standard is labeled with a second fluorophore that emits at a different wavelength. For example, Cy3 (570 nm) and Cy5 (670 nm) often are employed together in two-color microarray systems.

DNA microarray technology is well-developed, commercially available, and widely employed. Therefore, in performing disclosed methods, a person of ordinary skill in the art can use microarray technology to measure expression levels of genes encoding biomarker proteins without undue experimentation. DNA microarray chips, reagents (such as those for RNA or cDNA preparation, RNA or cDNA labeling, hybridization and washing solutions), instruments (such as microarray readers) and protocols are well known in the art and available from various commercial sources. Commercial vendors of microarray systems include Agilent Technologies (Santa Clara, CA) and Affymetrix (Santa Clara, CA), but other PCR systems can be used.

Quantitative PCR

The level of mRNA of the biomarkers of the invention can be measured using conventional quantitative reverse transcriptase polymerase chain reaction (qRT-PCR) technology. Advantages of qRT-PCR include sensitivity, flexibility, quantitative accuracy, and ability to discriminate between closely related mRNAs. Guidance concerning the processing of tissue samples for quantitative PCR is available from various sources, including manufacturers and vendors of commercial instruments and reagents for qRT-PCR (e.g., Qiagen (Valencia, CA) and Ambion (Austin, TX)). Instruments and systems for automated performance of qRT-PCR are commercially available and used routinely in many laboratories. An example of a well-known commercial system is the Applied Biosystems 7900HT Fast Real-Time PCR System (Applied Biosystems, Foster City, CA).

Once mRNA is isolated, the first step in gene expression measurement by RT-PCR is the reverse transcription of the mRNA template into cDNA, which is then exponentially amplified in a PCR reaction. Two commonly used reverse transcriptases are avilomyeloblastosis virus reverse transcriptase (AMV-RT) and Moloney murine leukemia virus reverse transcriptase (MMLV-RT). The reverse transcription reaction typically is primed with specific primers, random hexamers, or oligo(dT) primers. Suitable primers are commercially available, e.g., GeneAmp® RNA PCR kit (Perkin Elmer, Waltham, MA). The resulting cDNA product can be used as a template in the subsequent polymerase chain reaction.

The PCR step is carried out using a thermostable DNA-dependent DNA polymerase. The polymerase most commonly used in PCR systems is a *Thermus aquaticus* (Taq) polymerase. The selectivity of PCR results from the use of primers that are complementary to the DNA region targeted for amplification, i.e., regions of the cDNAs reverse transcribed from genes encoding proteins of interest. Therefore, when qRT-PCR is employed in the present invention, primers specific to each marker gene are based on the cDNA sequence of the gene. Commercial technologies such as SYBR® green or TaqMan® (Applied Biosystems, Foster City, CA) can be used in accordance with the vendor's instructions. Messenger RNA levels can be normalized for differences in loading among samples by comparing the levels of housekeeping genes such as beta-actin or GAPDH. The level of mRNA expression can be expressed relative to any single control sample such as mRNA from normal, non-tumor tissue or cells. Alternatively, it can be expressed relative to mRNA from a pool of tumor samples, or tumor cell lines, or from a commercially available set of control mRNA.

Suitable primer sets for PCR analysis of expression of genes NRG1 and/or the biomarkers of the invention can be designed and synthesized by one of skill in the art, without undue experimentation. Alternatively, PCR primer sets for practicing the present invention can be purchased from commercial sources, e.g., Applied Biosystems. PCR primers preferably are about 17 to 25 nucleotides in length. Primers can be designed to have a particular melting temperature (Tm), using conventional algorithms for Tm estimation. Software for primer design and Tm estimation are available commercially, e.g., Primer Express™ (Applied Biosystems), and also are available on the internet, e.g., Primer3 (Massachusetts Institute of Technology). By applying established principles of PCR primer design, a large number of different primers can be used to measure the expression level of any given gene, including NRG1 and the biomarkers of the invention.

RNAseq

RNAseq technology can also be used to measure mRNA expression levels of the biomarkers of the invention. RNAseq can perform study on gene expression differences at whole genome level, and has the following advantages of (1) directly determining the sequence of each transcript fragment, the accuracy of single nucleotide resolution, and there is no cross-reactivity and background noise issues caused by fluorescence analog signals of traditional microarray hybridizations (i.e., having digital signals); (2) capable of detecting as few as several copies of rare transcripts in the cell (i.e., with a very high sensitivity); (3) capable of performing whole genome analysis; (4) having a dynamic detection range higher than 6 orders of magnitude, and capable of identifying and quantifying rare transcripts and normal transcripts simultaneously (i.e., with a wide detection range). Based on the above advantages, RNAseq has become a powerful tool for accurate measurement of RNA expression levels.

The principle of RNAseq is: extracting RNAs, followed by pufication, reverse transcribing them into cDNAs, and then sequencing to obtain short reads; comparing the short reads to the corresponding position in the genome, and then splicing compared results at the gene level, the exon level and the transcription level. Finally, the data of the spliced results are statistically calculated, and the gene expression level of mRNAs is obtained after normalization. The comparison step, the splicing step, statistics step and the normalization step can be performed using various software known to those skilled in the art. For example, the comparison step can be performed by software such as BFAST, BOWTIE, GNUmap, CloudBurst, GMAP/GSNAP, RzaerS, SpliceMap, TopHat, MIRA, Soap, and the like; the splicing and statistical steps can be performed by software such as Cufflinks, ALEXA-seq, and the like; the normalization step can be carried out by software such as ERANGE, Myrna, and the like. The commonly used methods for normalizing RNAseq data include: RPKM (reads per kilobase of exon model per million mapped reads), FPKM (fragments per kilobase of exon model per million mapped reads) and TPM (tag per million).

Commonly used RNAseq platforms include Illumina GA/HiSeq, SOLID and Roche454.

qNPA™

In some embodiments, RNA analysis is performed using a technology that does not involve RNA extraction or isolation. One such technology is quantitative nuclease protection assay, which is commercially available under the name gNPA™ (High Throughput Genomics, Inc., Tucson, AZ). This technology can be advantageous when the tumor tissue samples to be analyzed are in the form of FFPE material. See, e.g., Roberts et al, 2007, Laboratory Investigation 87:979-997.

Protein Analysis

In other embodiments, the expression of the biomarkers of the invention can be detected at the protein level. Methods for measuring the expression level of the biomarkers of the invention at the protein level include enzyme linked immunosorbent assay (ELISA), IHC analysis, western blotting, immunofluorescence, and the like.

ELISA

Performing an ELISA requires at least one antibody against the biomarkers of the invention, i.e., the detection antibody. The following uses NRG1 as an example. NRG1 protein from a sample to be analyzed is immobilized on a solid support such as a polystyrene microtiter plate. This immobilization can be by non-specific binding, i.e., through adsorption to the surface. Alternatively, immobilization can be by specific binding, i.e., through binding of NRG1 from the sample by a capture antibody (anti-NRG1 antibody different from the detection antibody), in a "sandwich" ELISA. After the NRG1 is immobilized, the detection antibody is added, and the detection antibody forms a complex with the bound NRG1. The detection antibody is linked to an enzyme, either directly or indirectly, e.g., through a secondary antibody that specifically recognizes the detection antibody. Typically between each step, the plate, with bound NRG1, is washed with a mild detergent solution. Typical ELISA protocols also include one or more blocking steps, which involve use of a non-specifically-binding protein such as bovine serum albumin to block unwanted non-specific binding of protein reagents to the plate. After a final wash step, the plate is developed by addition of an appropriate enzyme substrate, to produce a visible signal, which indicates the quantity of NRG1 in the sample. The substrate can be, e.g., a chromogenic substrate or a fluorogenic substrate. ELISA methods, reagents and equipment are well-known in the art and commercially available.

Immunohistochemistry (IHC)

The presence and level of NRG1 in a tumor tissue sample, or clinical specimen, can be determined (e.g., visualized) by immunohistochemistry (IHC) or immunofluorescence (IF).

Because clinical specimens often are preserved as formalin fixed paraffin embedded (FFPE) blocks, IHC and IF are particularly useful for measuring NRG1 protein in clinical specimens. Assaying NRG1 by IHC or IF requires at least one antibody against NRG1. Anti-NRG1 antibodies suitable for IHC and IF are commercially available. For example, suitable antibodies can be purchased from R&D Systems (Minneapolis, MN), abeam (Cambridge, MA), Santa Cruz Biotechnology, Inc. (Santa Cruz, CA), or Novus Biologicals (Littleton, CO). Using standard techniques, the anti-NRG1 antibody can be used to detect the presence of NRG1 protein in thin sections, e.g., 5 micron sections, obtained from tumors, including FFPE sections and frozen tumor sections. Typically, the tumor sections are initially treated in such a way as to retrieve the antigenic structure of proteins that were fixed in the initial process of collecting and preserving the tumor material. Slides are then blocked to prevent non-specific binding by the anti-NRG1 detection antibody. The presence of NRG1 protein is then detected by binding of the anti-NRG1 antibody (primary antibody) to the NRG1 protein. The detection antibody (secondary antibody), which recognizes and binds to the primary antibody, is linked to a detectable enzyme or fluorophore. Typically, the tumor sections are washed and blocked with non-specific protein such as bovine serum albumin between steps. If the detection antibody is linked to a detectable enzyme, the slide is developed using an appropriate enzyme substrate to produce a visible signal. If the detection antibody is linked to a fluorophore, the slide is viewed by using a fluorescence microscope. The samples can be counterstained with hematoxylin.

Data Interpretation

Threshold expression level can be used to explain the expression levels of the biomarkers of the invention. For example, in an esophageal cancer sample, when an expression level of SDC2 and/or GNAZ is equal to or lower than its corresponding threshold expression level, the esophageal cancer is sensitive (responsive) to treatment with an ERBB3 inhibitor, e.g., an anti-ERBB3 antibody. Alternatively, when an expression level of SDC2 and/or GNAZ is higher than its corresponding threshold expression level, the esophageal cancer is resistant (non-responsive) to treatment with an ERBB3 inhibitor, e.g., an anti-ERBB3 antibody. For NRG1, NCF2, NOXA1, PTGES, and CARD6, if an expression level of one or more of them is equal to or higher than its corresponding threshold expression level, the esophageal cancer is sensitive (responsive) to treatment with an ERBB3 inhibitor, e.g., an anti-ERBB3 antibody. On the contrary, when an expression level of one or more of them is lower than its corresponding threshold expression level, the esophageal cancer is resistant (non-responsive) to treatment with an ERBB3 inhibitor, e.g., an anti-ERBB3 antibody.

Threshold Determination Analysis

Threshold expression levels of each biomarker can be determined by performing a threshold determination analysis. Preferably, threshold determination analysis includes receiver operator characteristic (ROC) curve analysis. ROC curve analysis is an established statistical technique, the application of which is within ordinary skill in the art. For a discussion of ROC curve analysis, see generally Zweig et al, 1993, "Receiver operating characteristic (ROC) plots: a fundamental evaluation tool in clinical medicine," Clin. Chem. 39:561-577; and Pepe, 2003, The statistical evaluation of medical tests or classification and prediction, Oxford Press, New York.

The dataset used for threshold determination analysis includes: (a) actual response data (response or non-response), and (b) an expression level of the biomarker of the invention for each tumor sample from a group of tumors. In certain embodiments, a threshold expression level is determined by measuring the expression level of biomarkers in tissue samples of tumors obtained from human esophageal cancer patients previously treated with an anti-ERBB3 inhibitor and shown to be sensitive to the anti-ERBB3 inhibitor and human esophageal cancer patients previously treated with an anti-ERBB3 inhibitor and shown to be resistant to anti-ERBB3 inhibitor.

The ROC curve analysis can be performed as follows (taking NRG1 as an example). Any sample with an NRG1 expression level greater than or equal to the threshold is classified as a responder (sensitive). Any sample with an NRG1 expression level lower than the threshold is classified as a non-responder (resistant). For every NRG1 expression level from a tested set of samples, "responders" and "non-responders" (hypothetical calls) are classified for the samples using that expression level as the threshold. This process enables calculation of TPR (y value) and FPR (x value) for each potential threshold, through comparison of hypothetical calls against the actual response data for the data set. Then an ROC curve is constructed by making a dot plot, using the TPR and FPR. If the ROC curve is above the diagonal from (0, 0) point to (1.0, 0.5) point, it shows that the NRG1 test result is a better test result than random.

The ROC curve can be used to identify the best threshold point. The best point is the one that yields the best balance between the cost of false positives weighed against the cost of false negatives. These costs need not be equal. The average expected cost (C) of classification at point x,y in the ROC space is determined by the following formula.

$$C=(1-p)\alpha^* x+p^*\beta(1-y)$$

wherein:
α=cost of a false positive,
β=cost of missing a positive (false negative), and
p=proportion of positive cases.

False positives and false negatives can be weighted differently by assigning different values for alpha and beta. For example, if it is decided to include more patients in the responder group at the cost of treating more patients who are non-responders, one can put more weight on α. In this case, it is assumed that the cost of false positive and false negative is the same (α equals to β). Therefore, the average expected cost of classification at point x,y in the ROC space is:

$$C'=(1-p)^* x+p^*(1-y).$$

The smallest C' can be calculated after using all pairs of false positive and false negative (x, y). The best threshold is calculated as the value of the (x, y) at C'.

In general, the higher the NRG1 expression level, the more likely a tumor is to be sensitive to an ERBB3 inhibitor, and the lower the NRG1 expression level, the more likely a tumor is to be resistant to an ERBB3 inhibitor. The above-mentioned threshold assay can also be used to determine the threshold expression levels of other biomarkers of the present invention.

Test Kits

Also disclosed is a diagnostic test kit comprising certain components for performing methods of the invention. A diagnostic test kit enhances convenience, speed and reproducibility in the performance of diagnostic assays. For example, in an exemplary qRT-PCR-based embodiment, a basic diagnostic test kit includes PCR primers for analyzing expression of the biomarkers of the present invention. In other embodiments, a more elaborate test kit contains not only PCR primers, but also buffers, reagents and detailed instructions for measuring the expression levels of the biomarkers, using PCR technology. In some embodiments, the kit includes a test protocol and all the consumable components needed for the test, except the RNA sample(s).

In an exemplary DNA microarray-based embodiment, a test kit includes a micro fluidic card (array) designed for use with a particular instrument. Optionally, the micro fluidic card is a custom made device designed specifically for measurement of the biomarkers of the present invention. Such custom micro fluidic cards are commercially available. For example, the TaqMan Array is a 384-well micro fluidic card (array) designed for use with the Applied Biosystems 7900HT Fast Real Time PCR System (Applied Biosystems, Foster City, CA). It is understood that additional probes can optionally be included on a fluidic card to measure the expression of one or more additional genes. Such additional genes may be included to serve as controls or standards, e.g., for data normalization, or may be otherwise informative.

In some embodiments, the test kit contains materials for determining content of the biomarkers of the present invention by IHC. An IHC kit, for example, may contain a primary antibody against the biomarkers of the present invention, and a secondary antibody conjugated to a reporter enzyme, e.g., horseradish peroxidase. In some embodiments, the secondary antibody is replaced with a conjugated polymer that specifically recognizes the primary antibody.

EXAMPLES

The invention is further illustrated by the following examples. The examples are provided for illustrative purposes only, and are not to be construed as limiting the scope or content of the invention in any way.

Example 1

Esophageal Cancer Xenograft Growth Response to CAN017

Evaluation of esophageal cancer response to CAN017 was performed as follows.

Fresh tumor tissue obtained from esophageal cancer patients after surgery was divided into small tumor masses and inoculated subcutaneously in immunodeficient mice (BALB/c nude mice), and the tumor growth status was regularly observed. After the tumor reached a certain volume, the mice were sacrificed in a humanitarian manner, and the tumor was inoculated subcutaneously into new BALB/c nude mice. Growth curves were plotted based on tumor growth status. Meanwhile, tumor samples were collected, frozen and observed for tumor tissue, and then resuscitated when needed for next generation inoculation. After several generations of optimization, a xenograft model of esophageal cancer was successfully established. This model was subcutaneously inoculated to the right side of 9-11 week old female BALB/c nude mice, and the diameter of the inoculated model was 2-3 mm.

Tumor measurements were taken twice weekly using vernier calipers. Tumor volume was calculated using the formula: width×width×length/2. When tumors reached approximately 158 mm$^3$, the mice were randomized into three groups, with each group of 10 mice each. One group received normal saline, one group received the hIgG control (20 mg/kg body weight), and the other group received CAN017 (20 mg/kg body weight). The drug was administered every three days by intraperitoneal injection for 3 weeks. Tumor volume and mice weight were recorded twice a week. Tumor growth was expressed as a percentage of inhibition compared to the normal saline and the control.

In total, 20 xenograft models of esophageal cancer were treated with CAN017 (10 mice per model), and the statistical results are shown in FIG. 12. The average inhibition percentage of CAN017 on all 20 xenograft models was about 43.6%, while the average inhibition percentage of control hIgG on all 20 xenograft models was −5.5%. Statistical analysis showed that compared with hIgG, the inhibition percentage of CAN017 on xenograft models of esophageal cancer reached a significant level (P<0.01). These results indicate that CAN017 can effectively inhibit the growth of esophageal cancer tumors.

Further analysis of the response of a single esophageal cancer xenograft model to CAN017 found that the response was varied, ranging from −40% tumor growth inhibition (TGI) to tumor regression. "Tumor regression" means that a tumor is smaller at the end of the evaluation period compared to the size of the tumor at the beginning of the evaluation period prior to treatment. Based on the tumor growth inhibition achieved, responders (defined as those with TGI>70%) and non-responders (defined as those with TGI<70%) were identified. Of the 20 tumors evaluated, 9 were found to be responders, and 11 were found to be non-responders (Table 1). These groups enabled the identification of a molecular marker for CAN017 responsiveness.

TABLE 1

Results of CAN017 on tumor growth inhibition in 20 esophageal cancer xenograft models and the average mRNA expression level of NRG1

| Model Nos | Average TGI (%) | Average NRG1 | Model Nos | Average TGI (%) | Average NRG1 |
|---|---|---|---|---|---|
| ES0026 | 7 | 3.0 | ES0199 | 106 | 3.3 |
| ES0190 | 78 | 3.6 | ES0191 | 116.6 | 2.1 |
| ES0136 | −40 | 0.4 | ES6824 | 15 | 0.2 |
| ES0141 | 74 | 2.9 | ES0214 | 135 | 3.5 |
| ES0147 | 101 | 3.0 | ES0215 | −2 | 4.0 |
| ES0148 | 13 | 0.3 | ES0218 | 25 | 1.2 |
| ES0184 | 72.5 | 4.0 | ES0219 | 24 | 0.6 |
| ES0176 | 80 | 3.3 | ES0630 | −6 | 0.9 |
| ES2356 | 31 | 3.7 | ES2263 | 1 | 1.1 |
| ES0042 | 109.4 | 3.8 | ES2267 | 16 | 0.1 |

Example 2

Expression Level of Biomarker NRG1 and Threshold Determination

The expression level of NRG1 was determined by RNAseq according to the following protocol: after quickly freezing the tumor tissue, RNA was extracted and purified with RNeasy Mini Kit (Qiagen, No. 74106), then the purified RNA was pre-processed according to TruSeq™ RNA Sample Preparation Guide (Illumina, No. RS-930-2001), and then sequenced on HiSeq X System (Illumina) according to the manufacturer's instructions. The resulting data is normalized with FPKM (expressed by log 2 (FPKM+1) value) to obtain the expression level of NRG1.

NRG1 expression levels were measured in 20 esophageal cancer xenograft models (average 10 mice per model) before treatment with CAN017. The average NRG1 expression level of each model is shown in Table 1. A receiver operator characteristic (ROC) curve was generated based on the obtained NRG1 expression levels to determine an NRG1 expression threshold used for predicting CAN017 tumor response. ROC analysis results showed that the threshold expression level of NRG1 was 2.05. That is, expression levels higher than this threshold predict CAN017 tumor response. In fact, the expression level of NRG1 is consistent with the CAN017 response in most of the xenograft models tested (i.e., a threshold expression level of 2.05 or higher was indicated to respond to CAN017; a threshold expression level below 2.05 was indicated not to respond to CAN017). However, in esophageal cancer xenograft models ES0026, ES2356, and ES0215, although the expression level of NRG1 was higher than the threshold expression level, these three xenograft models did not actually respond to CAN017. Accordingly, although NRG1 as a biomarker can predict whether esophageal cancer will respond to treatment with anti-ERBB3 antibodies to some extent, the effectiveness of using NRG1 alone for prediction is limited.

Example 3

Relationship Between Expression Level of Biomarker of the Invention and CAN017 Response According to the RNAseq method described in Example 2, the expression levels of SDC2, GNAZ, PTGES, NCF2, NOX1, and CARD6 in 20 esophageal cancer xenograft models (average 10 mice per model) were measured, and the threshold expression level of each biomarker was determined by the ROC curve. The results of the threshold expression levels of each biomarker are as follows: the threshold expression level of SDC2 is 4.9, the threshold expression level of GNAZ is 1.1, the threshold expression level of PTGES is 2.75, the threshold expression level of NCF2 is 2.6, the threshold expression level of NOX1 is 2.7, and the threshold expression level of CARD6 is 1.0.

CAN017 tumor growth inhibition in these models was plotted against the average expression levels of each biomarker within each model, and the significance of the correlation between the expression level of each biomarker and the tumor growth inhibition was tested by regression analysis. The results are shown in FIGS. 13-18.

Figure 14:
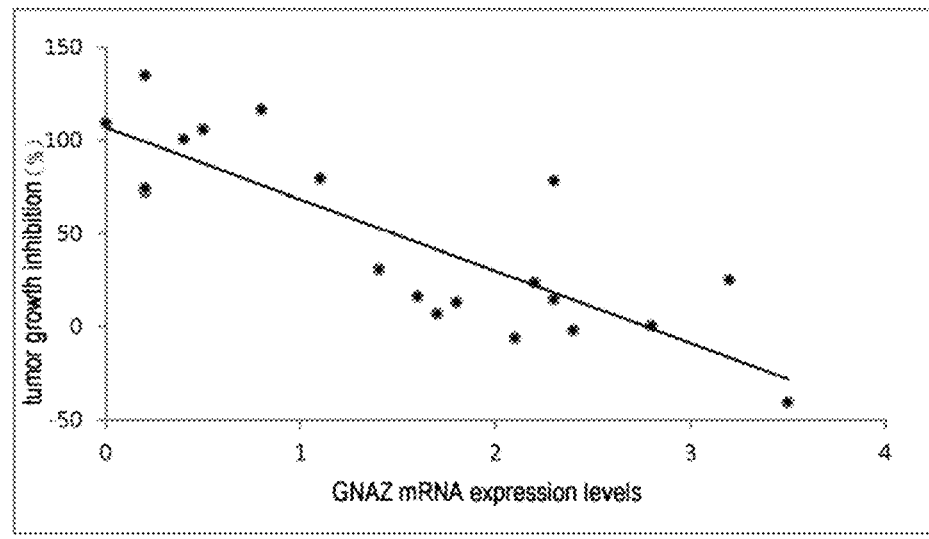
FIG. 14 (upper panel) is a scatter plot with a linear regression trend line showing the relationship between the in vivo efficacy of CAN017 in 20 xenograft models (expressed as percentage of tumor growth inhibition (TGI)) and mRNA expression levels of GNAZ. The 20 data points are represented by (●), wherein the solid line indicates the correlation between the mRNA expression levels of GNAZ and tumor growth inhibition.
Figure 15:
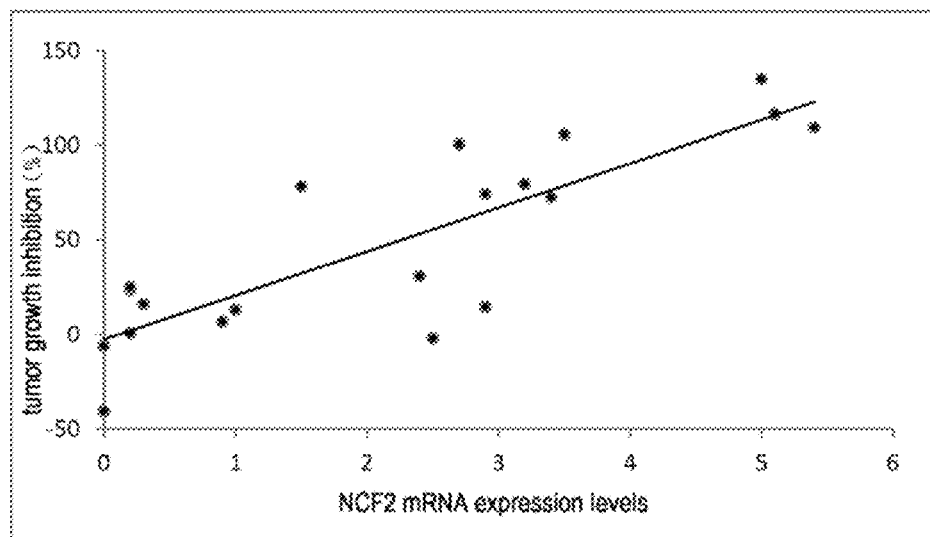
FIG. 15 (upper panel) is a scatter plot with a linear regression trend line showing the relationship between the in vivo efficacy of CAN017 in 20 xenograft models (expressed as percentage of tumor growth inhibition (TGI)) and mRNA expression levels of NCF2. The 20 data points are represented by (●), wherein the solid line indicates the correlation between the mRNA expression levels of NCF2 and tumor growth inhibition.
Figure 16:
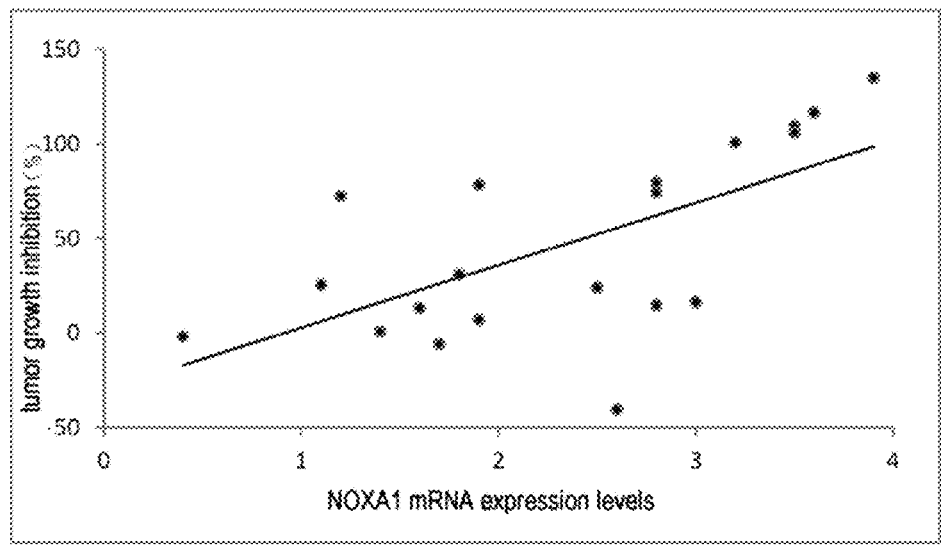
FIG. 16 (upper panel) is a scatter plot with a linear regression trend line showing the relationship between the in vivo efficacy of CAN017 in 20 xenograft models (expressed as percentage of tumor growth inhibition (TGI)) and mRNA expression levels of NOXA1. The 20 data points are represented by (●), wherein the solid line indicates the correlation between the mRNA expression levels of NOXA1 and tumor growth inhibition.
Figure 17:
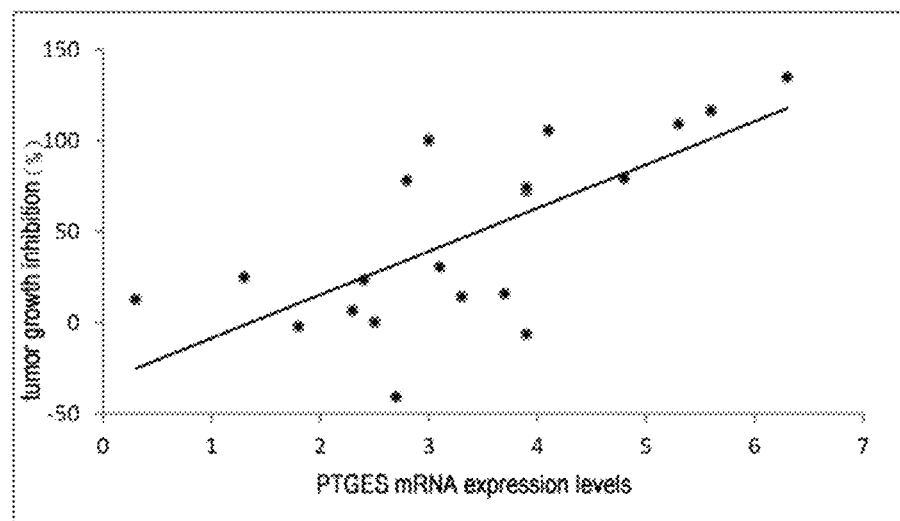
FIG. 17 (upper panel) is a scatter plot with a linear regression trend line showing the relationship between the in vivo efficacy of CAN017 in 20 xenograft models (expressed as percentage of tumor growth inhibition (TGI)) and mRNA expression levels of PTGES. The 20 data points are represented by (●), wherein the solid line indicates the correlation between the mRNA expression levels of PTGES and tumor growth inhibition.
Figure 18:
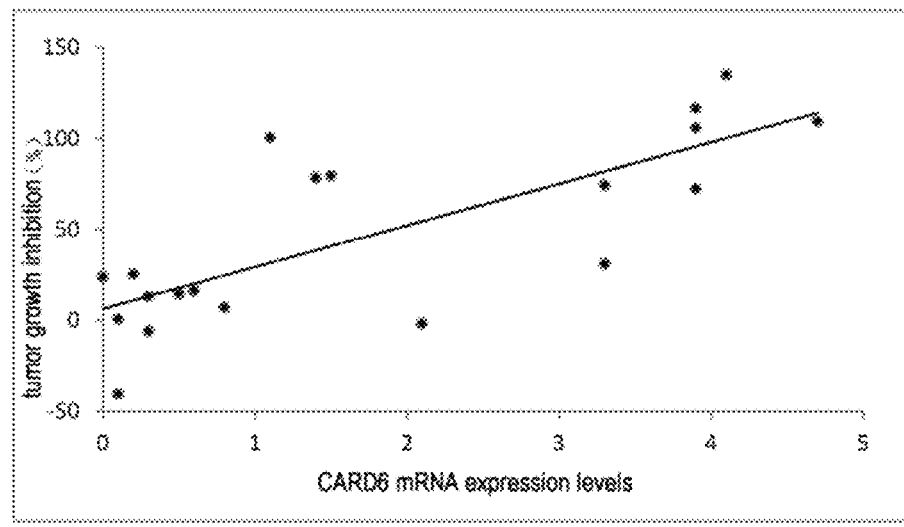
FIG. 18 (upper panel) is a scatter plot with a linear regression trend line showing the relationship between the in vivo efficacy of CAN017 in 20 xenograft models (expressed as percentage of tumor growth inhibition (TGI)) and mRNA expression levels of CARD6. The 20 data points are represented by (●), wherein the solid line indicates the correlation between the mRNA expression levels of CARD6 and tumor growth inhibition.

Specifically, as shown in FIG. 13, a negative correlation was observed between tumor growth inhibition and SDC2 expression. More specifically, increased tumor growth inhibition after treatment with CAN017 correlated with decreased SDC2 expression. Regression analysis found that this correlation was highly statistically significant (significance $F<0.05$). FIG. 14 showed that a negative correlation was observed between tumor growth inhibition and GNAZ expression. That is, tumor growth inhibition decreases with increasing GNAZ expression levels. This correlation was also found to be statistically significant (significance $F<0.05$).

FIGS. 15-18 showed that positive correlations were observed between tumor growth inhibition and NCF2, NOXA1, PTGES, and CARD6 expressions. That is, tumor growth inhibition increases with increasing expression levels of these biomarkers. These correlations were also found to be statistically significant (significance $F<0.05$).

The above results indicate that the expression levels of each of the biomarkers SDC2, GNAZ, PTGES, NCF2, NOX1, and CARD6 of the present invention are significantly correlated with tumor growth inhibition. Therefore, these biomarkers can be used to predict whether a tumor will respond to CAN017 treatment.

Example 4

Esophageal Cancer Xenograft Model Response to Anti-ERBB3 Antibody CAN017

According to the threshold expression level of each biomarker obtained in Example 3, a xenograft model predicted to respond to CAN017 was selected, and a xenograft model predicted to not respond to CAN017 was selected. Specifically, for SDC2 with a threshold expression level of 4.9, xenograft models ES0195 and ES0204 with high expressions (SDC2 expression levels were 5.8 and 5.2, respectively) were selected, and the models were predicted to not respond to CAN017; at the same time, xenografts models ES0042 and ES0190 with low expressions (SDC2 expression levels were 0.6 and 4.3, respectively) were selected, and the models were predicted to respond to CAN017. Similarly, for GNAZ with a threshold expression level of 1.1, xenograft models ES0201 and ES2411 with high expressions (GNAZ expression levels were 1.3 and 1.9, respectively) were selected, and the models were predicted to not respond to CAN017; at the same time, xenografts models ES0184 and ES0199 with low expressions (GNAZ expression levels were 0.2 and 0.5, respectively) were selected, and the models were predicted to respond to CAN017. For NCF2 with a threshold expression level of 2.6, xenograft models ES0191 and ES0176 with high expressions (NCF2 expression levels were 5.1 and 3.2, respectively) were selected, and the models were predicted to respond to CAN017; at the same time, xenografts models ES0204 and ES0026 with low expressions (NCF2 expression levels were 0.1 and 0.9, respectively) were selected, and the models were predicted to not respond to CAN017. For NOXA1 with a threshold expression level of 2.7, xenograft models ES2311 and ES0214 with high expressions (NOXA1 expression levels were 2.98 and 3.9, respectively) were selected, and the models were predicted to respond to CAN017; at the same time, xenografts models ES11087 and ES0148 with low expressions (NOXA1 expression levels were 2.14 and 1.6, respectively) were selected, and the models were predicted to not respond to CAN017. For PTGES with a threshold expression level of 2.75, xenograft models ES0159 and ES0141 with high expressions (PTGES expression levels were 5.69 and 3.9, respectively) were selected, and the models were predicted to respond to CAN017; at the same time, xenografts models ES10084 and ES0172 with low expressions (PTGES expression levels were 0.55 and 1.7, respectively) were selected, and the models were predicted to not respond to CAN017. For CARD6 with a threshold expression level of 1.0, xenograft models ES11069 and ES0147 with high expressions (CARD6 expression levels were 4.01 and 1.0, respectively) were selected, and the models were predicted to respond to CAN017; at the same time, xenografts models ES0212 and ES0136 with low expressions (CARD6 expression levels were 0.09 and 0.1, respectively) were selected, and the models were predicted to not respond to CAN017.

According to the method described in Example 1, the above-selected xenograft models (5 mice per model) were treated with 20 mg/kg antibody CAN017, and the tumor growth inhibition of each model was calculated after 3 weeks. The results are shown in Table 3.

TABLE 3

Statistics of results of xenograft
models treated with antibody CAN017

| Biomarkers | Threshold | Model Nos. (expression level) | TGI (%) |
|---|---|---|---|
| SDC2 | 4.9 | ES0195 (5.8) | 44.9 |
|  |  | ES0204 (5.2) | −16.5 |
|  |  | ES0042 (0.6) | 109.4 |
|  |  | ES0190 (4.3) | 78.4 |
| GNAZ | 1.1 | ES0201 (1.3) | 24.1 |
|  |  | ES2411 (1.9) | 45.1 |
|  |  | ES0184 (0.2) | 72.5 |
|  |  | ES0199 (0.5) | 105.9 |
| NCF2 | 2.6 | ES0191 (5.1) | 116.6 |
|  |  | ES0176 (3.2) | 79.6 |
|  |  | ES0204 (0.1) | −16.5 |
|  |  | ES0026 (0.9) | 6.8 |
| NOXA1 | 2.7 | ES2311 (2.98) | 85.2 |
|  |  | ES0214 (3.9) | 135.1 |
|  |  | ES11087 (2.14) | 23.6 |
|  |  | ES0148 (1.6) | 13.1 |
| PTGES | 2.75 | ES0159 (5.69) | 95.3 |
|  |  | ES0141 (3.9) | 74.4 |
|  |  | ES10084 (0.55) | 46.4 |
|  |  | ES0172 (1.7) | 44.6 |
| CARD6 | 1.0 | ES11069 (4.01) | 77.8 |
|  |  | ES0147 (1.1) | 110.6 |
|  |  | ES0212 (0.09) | 32.6 |
|  |  | ES0136 (0.1) | −40.5 |

The above data indicates that tumor response to treatment with CAN017 can be effectively predicted by measuring the expression levels of SDC2, GNAZ, PTGES, NCF2, NOX1, and CARD6.

Example 5

Use of the Biomarkers of the Present Invention in Combination with NRG1

The inventors also found that the use of the biomarkers of the present invention in combination with NRG1 can further improve the accuracy for predicting whether a tumor responds to CAN017 treatment. As mentioned above, NRG1 alone as a marker cannot accurately predict whether esophageal cancer xenograft models ES0026, ES2356, and ES0215 will respond (i.e., although the expression level of NRG1 is higher than the threshold, it does not respond after treatment with CAN017 (TGI<70%)). The inventors determined the expression levels of the biomarkers of the present invention in these three models, and the results were shown in Table 4 below.

TABLE 4

Expression levels of biomarkers in xenograft models ES0026, ES2356 and ES0215.

| Model Nos. | SDC2 | GNAZ | NCF2 | NOXA1 | PTGES | CARD6 |
|---|---|---|---|---|---|---|
| ES0026 | 6.1 | 1.7 | 0.9 | 1.9 | 2.3 | 0.8 |
| ES2356 | 7.7 | 1.4 | 2.4 | 1.8 | 3.1 | 3.3 |
| ES0215 | 8.1 | 2.4 | 2.5 | 0.4 | 1.8 | 2.1 |

The above data shows that in these three models, both the expression levels of SDC2 and GNAZ are higher than their corresponding threshold expression levels, and both the expression levels of NCF2 and NOXA1 are lower than their corresponding threshold expression levels, indicating that when these biomarkers are used for prediction, xenograft models ES0026, ES2356, and ES0215 will be predicted to not respond to CAN017 treatment. In other words, when NRG1 is higher than its threshold expression level, measurement of the expression level of the biomarker of the invention can further improve the accuracy for predicting whether a tumor responds to CAN017 treatment (for example, in the case of xenograft models ES0026, ES2356, and ES0215, it is considered that the biomarker of the present invention can accurately predict that they will not respond to CAN017 treatment).

Figure 19:
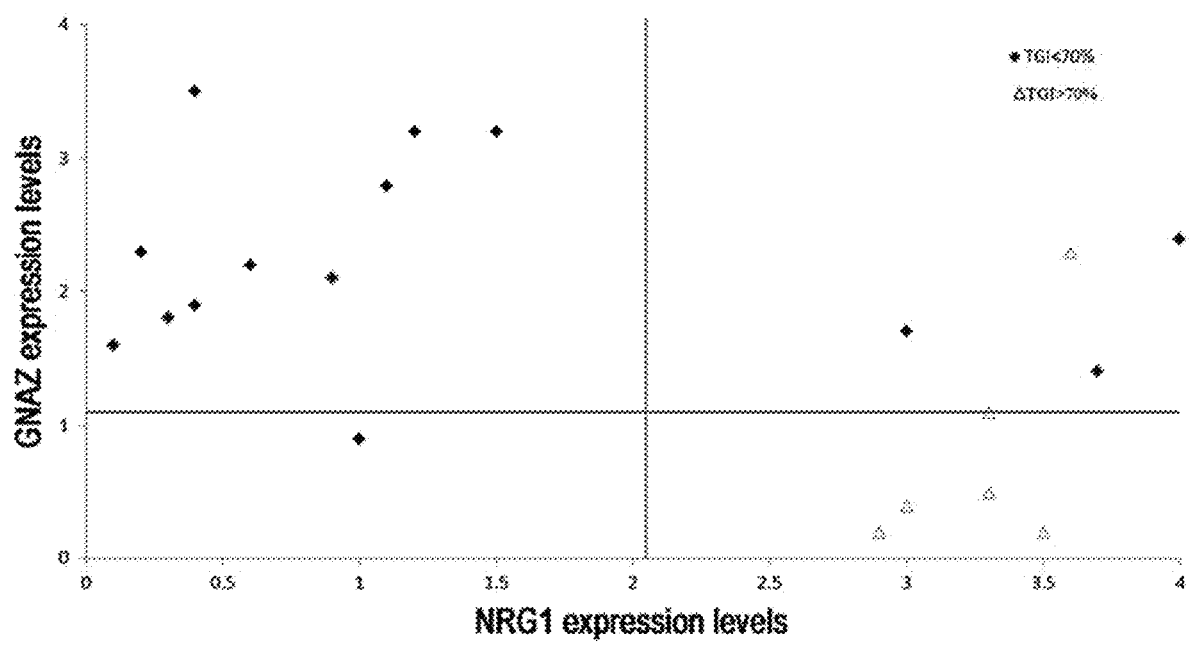
FIG. 19 is a schematic diagram showing the relationship between the expression levels of GNAZ and NRG1 and the percentage of tumor growth inhibition (TGI). The solid line parallel to the Y axis indicates the threshold expression level of NRG1 of 2.05, and the solid line parallel to the X axis indicates the threshold expression level of GNAZ of 1.1. ♦ means TGI <70%; Δ means TGI>70%.

The inventors also found that when at least one biomarker positively related to TGI and one biomarker negatively related to TGI are used at the same time, the accuracy of prediction will be further improved. Among 20 esophageal cancer xenograft models, the accuracy of prediction wherein NRG1 alone was used as a marker was 85%, and the accuracy of prediction wherein GNAZ alone was used as a marker was 90%. However, when NRG1 and GNAZ were both used as markers for prediction, the accuracy rate was 95% (FIG. 19).

Example 6

Esophageal Cancer Xenograft Model Response to Anti-ERBB3 Antibody 11G01

In order to validate this prediction method for response to other anti-ERBB3 antibodies, the 12 esophageal cancer xenograft models selected in Example 4 were treated with an anti-ERBB3 antibody (antibody 11G01) with a mechanism of action different from CAN017. Specifically, the 12 esophageal cancer xenograft models were treated with 20 mg/kg antibody 11G01 in the manner described in Example 1, and the tumor growth inhibition percentages of each model were calculated after 3 weeks. The results are similar to those of Example 4 (that is, the tumor response to the antibody predicted based on each biomarker is consistent with the actual observed tumor response to the antibody, and the data is not shown). This indicates that the biomarker of the present invention can effectively predict the esophageal cancer response to treatment with other anti-ERBB3 antibodies having a mechanism of action different from CAN017.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. Thus, the scope of the invention is indicated by the appended claims rather than by the foregoing description, and all changes that come within the meaning and range of equivalency of the claims are intended to be embraced therein.

What is claimed is:

1. A method for determining that an esophageal cancer is sensitive to treatment with an anti-ERBB3 antibody, and treating the esophageal cancer, the method comprising:
   (a) measuring an expression level of SDC2 in an esophageal cancer sample from a subject;
   (b) comparing the expression level of the SDC2 in the esophageal cancer sample with a threshold expression level of SDC2, the threshold expression level of SDC2 having been determined according to a threshold determination analysis of a first dataset of esophageal cancer samples;
   (c) determining by the comparison that the expression level of the SDC2 in the esophageal cancer sample is equal to or lower than the threshold expression level of SDC2 and thereby determining that the esophageal cancer is sensitive to treatment with an anti-ERBB3 antibody; and (d) following the determination that the esophageal cancer is sensitive to treatment with the anti-ERBB3 antibody, administering the anti-ERBB3 antibody to the subject.

2. The method of claim 1, further comprising:
measuring an expression level of NRG1 in the esophageal cancer sample;
comparing the expression level of the NRG1 in the esophageal cancer sample with a threshold expression level of NRG1, the threshold expression level of NRG1 having been determined according to a threshold determination analysis of a second dataset of esophageal cancer samples; and
determining by the comparison that the expression level of the NRG1 in the esophageal cancer sample is equal to or higher than the threshold expression level of NRG1.

3. The method of claim 1, wherein the anti-ERBB3 antibody comprises
(i) an immunoglobulin heavy chain variable region comprising a $CDR_{H1}$ comprising the amino acid sequence of SEQ ID NO: 1, a $CDR_{H2}$ comprising the amino acid sequence of SEQ ID NO: 2, and a $CDR_{H3}$ comprising the amino acid sequence of SEQ ID NO: 3; and
(ii) an immunoglobulin light chain variable region comprising a $CDR_{L1}$ comprising the amino acid sequence of SEQ ID NO: 4, a $CDR_{L2}$ comprising the amino acid sequence of SEQ ID NO: 5, and a $CDR_{L3}$ comprising the amino acid sequence of SEQ ID NO: 6.

4. The method of claim 1, wherein the anti-ERBB3 antibody comprises an immunoglobulin heavy chain variable region comprising the amino acid sequence of SEQ ID NO: 7, and an immunoglobulin light chain variable region comprising the amino acid sequence of SEQ ID NO: 8.

5. The method of claim 1, wherein the anti-ERBB3 antibody comprises an immunoglobulin heavy chain comprising the amino acid sequence of SEQ ID NO: 9, and an immunoglobulin light chain comprising the amino acid sequence of SEQ ID NO: 10.

6. The method of claim 1, wherein the expression level of the SDC2 in the esophageal cancer sample is the protein expression level of the SDC2.

7. The method of claim 1, wherein the expression level of the SDC2 in the esophageal cancer sample is the mRNA expression level of the SDC2.

8. The method of claim 1, further comprising:
measuring an expression level of GNAZ in the esophageal cancer sample;
comparing the expression level of the GNAZ in the esophageal cancer sample with a threshold expression level of GNAZ, the threshold expression level of GNAZ having been determined according to a threshold determination analysis of a third dataset of esophageal cancer samples; and
determining by the comparison that the expression level of the GNAZ in the esophageal cancer sample is equal to or lower than the threshold expression level of GNAZ.

9. The method of claim 1, further comprising:
measuring an expression level of PTGES, NCF2, MOXA1, or CARD6 in the esophageal cancer sample;
comparing the expression level of the PTGES, NCF2, NOXA1, or CARD6 in the esophageal cancer sample with a threshold expression level of PTGES, NCF2, NOXA1, or CARD6, respectively, the threshold expression level of PTGES, NCF2, NOXA1, or CARD6 having been determined according to a threshold determination analysis of a fourth dataset of esophageal cancer samples; and
determining by the comparison that the expression level of the PTGES, NCF2, NOXA1, or CARD6 in the esophageal cancer sample is equal to or higher than the threshold expression level of PTGES, NCF2, NOXA1, or CARD6, respectively.

\* \* \* \* \*

SEQUENCE LISTING

<160> NUMBER OF SEQ ID NOS: 62

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ile Ser Asp Gly Gly Thr Tyr Thr Tyr Tyr Pro Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Trp Gly Asp Tyr Asp Gly Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Glu Ile Ser Gly Tyr Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ala Ser Thr Leu Asp Ser
1               5

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Leu Gln Tyr Asp Ser Tyr Pro Tyr Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Arg Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gln Gly Thr Lys Leu Glu Ile Lys
            100                 105

<210> SEQ ID NO 9
<211> LENGTH: 471
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Ala Met Ser Trp Ile Arg Gln Ala Pro Gly
    50                  55                  60

Lys Gly Leu Glu Trp Val Ser Thr Ile Ser Asp Gly Gly Thr Tyr Thr
65                  70                  75                  80

Tyr Tyr Pro Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380
```

```
Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 10
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Glu Ile Ser Gly Tyr Leu Ser Trp Tyr Gln Gln Lys Pro Gly Lys
        50                  55                  60

Ala Pro Lys Arg Leu Ile Tyr Ala Ala Ser Thr Leu Asp Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
                100                 105                 110

Tyr Asp Ser Tyr Pro Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 11
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 11

Ser His Trp Leu His
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Asp Pro Ser Asp Phe Tyr Ser Asn Tyr Asn Gln Asn Phe Lys
1               5                   10                  15

Gly

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Leu Ser Gly Asp Tyr Ala Met Asp Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Ser Gln Ser Ile Val His Ser Asn Gly Asn Thr Tyr Leu Glu
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Val Ser Asn Arg Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

```
Phe Gln Gly Ser Tyr Val Pro Trp Thr
 1               5
```

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Gln Gln Pro Gly Ala Glu Leu Val Arg Pro Gly Thr
 1               5                  10                  15

Ser Val Lys Leu Ser Cys Lys Ala Ser Gly Tyr Thr Phe Thr Ser His
                20                  25                  30

Trp Leu His Trp Val Lys Gln Arg Pro Gly Gln Gly Leu Glu Trp Ile
            35                  40                  45

Gly Val Leu Asp Pro Ser Asp Phe Tyr Ser Asn Tyr Asn Gln Asn Phe
        50                  55                  60

Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Gly Leu Leu Ser Gly Asp Tyr Ala Met Asp Tyr Trp Gly Gln
                100                 105                 110

Gly Thr Ser Val Thr Val Ser Ser
            115                 120
```

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Asp Val Leu Met Thr Gln Ile Pro Leu Ser Leu Pro Val Ser Leu Gly
 1               5                  10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Ser Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
                100                 105                 110
```

<210> SEQ ID NO 19
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Gly Trp Ser Cys Ile Ile Val Leu Leu Val Ser Thr Ala Thr Gly
1               5                   10                  15

Val His Ser Gln Val Gln Leu Gln Gln Pro Gly Ala Glu Leu Val Arg
            20                  25                  30

Pro Gly Thr Ser Val Lys Leu Ser Cys Lys Ala Ser Gly Tyr Thr Phe
        35                  40                  45

Thr Ser His Trp Leu His Trp Val Lys Gln Arg Pro Gly Gln Gly Leu
    50                  55                  60

Glu Trp Ile Gly Val Leu Asp Pro Ser Asp Phe Tyr Ser Asn Tyr Asn
65                  70                  75                  80

Gln Asn Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Leu Leu Ser Gly Asp Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Pro Ser Ser Thr Trp Pro Ser Gln Thr Val Thr Cys Asn Val Ala
210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Asp Ile Ser Lys Asp Asp Pro Glu
        275                 280                 285

Val Gln Phe Ser Trp Phe Val Asp Asp Val Glu Val His Thr Ala Gln
    290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
        355                 360                 365

Pro Pro Lys Glu Gln Met Ala Lys Asp Lys Val Ser Leu Thr Cys Met
    370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415
```

Asp Gly Ser Tyr Phe Val Tyr Ser Lys Leu Asn Val Gln Lys Ser Asn
              420                 425                 430

Trp Glu Ala Gly Asn Thr Phe Thr Cys Ser Val Leu His Glu Gly Leu
              435                 440                 445

His Asn His His Thr Glu Lys Ser Leu Ser His Ser Pro Gly Lys
        450                 455                 460

<210> SEQ ID NO 20
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
              20                  25                  30

Ser Leu Gly Asp Gln Ala Ser Ile Ser Cys Arg Ser Ser Gln Ser Ile
          35                  40                  45

Val His Ser Asn Gly Asn Thr Tyr Leu Glu Trp Tyr Leu Gln Lys Pro
    50                  55                  60

Gly Gln Ser Pro Lys Ser Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Phe Gly Leu Ser Val Gly
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Ile Trp Trp Asp Asp Asp Lys Tyr Tyr Asn Pro Ala Leu Lys Ser
1               5                   10                  15

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Gly Ala Asp Ala Leu Pro Phe Asp Tyr
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Ser Lys Ser Leu Leu His Ser Asn Gly Asn Thr Tyr Leu Tyr
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Met Ser Asn Leu Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Gln His Leu Glu Tyr Pro Phe Thr
1               5

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Thr Leu Lys Glu Ser Gly Pro Gly Ile Leu Arg Pro Ser Gln
1               5                   10                  15

Thr Leu Ser Leu Thr Cys Ser Phe Ser Gly Phe Ser Leu Ser Thr Phe
            20                  25                  30

Gly Leu Ser Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ile Gly Ala Asp Ala Leu Pro Phe Asp Tyr Trp Gly Gln
            100                 105                 110

Gly Thr Leu Thr Val Ser Ser
        115                 120

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Leu Thr Gln Thr Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 29
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Arg
            20                  25                  30

Pro Ser Gln Thr Leu Ser Leu Thr Cys Ser Phe Ser Gly Phe Ser Leu
        35                  40                  45

-continued

```
Ser Thr Phe Gly Leu Ser Val Gly Trp Ile Arg Gln Pro Ser Gly Lys
    50                  55                  60
Gly Leu Glu Trp Leu Ala His Ile Trp Trp Asp Asp Lys Tyr Tyr
 65              70                  75                  80
Asn Pro Ala Leu Lys Ser Arg Leu Thr Ile Ser Lys Asp Thr Ser Lys
                85                  90                  95
Asn Gln Val Phe Leu Lys Ile Ala Asn Val Asp Thr Ala Asp Thr Ala
                100                 105                 110
Thr Tyr Tyr Cys Ala Arg Ile Gly Ala Asp Ala Leu Pro Phe Asp Tyr
            115                 120                 125
Trp Gly Gln Gly Thr Thr Leu Thr Val Ser Ser Ala Lys Thr Thr Pro
    130                 135                 140
Pro Ser Val Tyr Pro Leu Ala Pro Gly Cys Gly Asp Thr Thr Gly Ser
145                 150                 155                 160
Ser Val Thr Ser Gly Cys Leu Val Lys Gly Tyr Phe Pro Glu Pro Val
                165                 170                 175
Thr Val Thr Trp Asn Ser Gly Ser Leu Ser Ser Val His Thr Phe
                180                 185                 190
Pro Ala Leu Leu Gln Ser Gly Leu Tyr Thr Met Ser Ser Ser Val Thr
            195                 200                 205
Val Pro Ser Ser Thr Trp Pro Ser Gln Thr Val Thr Cys Ser Val Ala
    210                 215                 220
His Pro Ala Ser Ser Thr Val Asp Lys Lys Leu Glu Pro Ser Gly
225                 230                 235                 240
Pro Ile Ser Thr Ile Asn Pro Cys Pro Pro Cys Lys Glu Cys His Lys
                245                 250                 255
Cys Pro Ala Pro Asn Leu Glu Gly Gly Pro Ser Val Phe Ile Phe Pro
            260                 265                 270
Pro Asn Ile Lys Asp Val Leu Met Ile Ser Leu Thr Pro Lys Val Thr
    275                 280                 285
Cys Val Val Val Asp Val Ser Glu Asp Asp Pro Asp Val Gln Ile Ser
290                 295                 300
Trp Phe Val Asn Asn Val Glu Val His Thr Ala Gln Thr Gln Thr His
305                 310                 315                 320
Arg Glu Asp Tyr Asn Ser Thr Ile Arg Val Val Ser Thr Leu Pro Ile
                325                 330                 335
Gln His Gln Asp Trp Met Ser Gly Lys Glu Phe Lys Cys Lys Val Asn
            340                 345                 350
Asn Lys Asp Leu Pro Ser Pro Ile Glu Arg Thr Ile Ser Lys Ile Lys
            355                 360                 365
Gly Leu Val Arg Ala Pro Gln Val Tyr Thr Leu Pro Pro Pro Ala Glu
    370                 375                 380
Gln Leu Ser Arg Lys Asp Val Ser Leu Thr Cys Leu Val Val Gly Phe
385                 390                 395                 400
Asn Pro Gly Asp Ile Ser Val Glu Trp Thr Ser Asn Gly His Thr Glu
                405                 410                 415
Glu Asn Tyr Lys Asp Thr Ala Pro Val Leu Asp Ser Asp Gly Ser Tyr
            420                 425                 430
Phe Ile Tyr Ser Lys Leu Asn Met Lys Thr Ser Lys Trp Glu Lys Thr
            435                 440                 445
Asp Ser Phe Ser Cys Asn Val Arg His Glu Gly Leu Lys Asn Tyr Tyr
450                 455                 460
Leu Lys Lys Thr Ile Ser Arg Ser Pro Gly Lys
```

<210> SEQ ID NO 30
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Arg Cys Leu Ala Glu Phe Leu Gly Leu Leu Val Leu Trp Ile Pro
1               5                   10                  15

Gly Ala Ile Gly Asp Ile Val Leu Thr Gln Thr Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ser Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Arg Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp His Ile Ile His
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 32

Tyr Ile Tyr Pro Arg Asp Gly Tyr Ile Lys Tyr Asn Glu Lys Phe Lys
1               5                   10                  15

Gly

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Tyr Tyr Tyr Ala Met Asp Tyr
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Ser Gln Ser Ile Val His Ser Ile Gly Asn Thr Tyr Leu Glu
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gln Gly Ser His Val Pro Phe Thr
1               5

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
                20                  25                  30

Ile Ile His Trp Met Lys Gln Arg Pro Glu Gln Gly Leu Glu Trp Ile
            35                  40                  45

Gly Tyr Ile Tyr Pro Arg Asp Gly Tyr Ile Lys Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Val Asn Ser Leu Thr Ser Glu Asp Ser Ala Val Tyr Phe Cys
                85                  90                  95

```
Ala Arg Gly Tyr Tyr Tyr Ala Met Asp Tyr Trp Gly Gln Gly Thr Ser
            100                 105                 110

Val Thr Val Ser Ser
        115

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Ile Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Glu Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 38
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Glu Trp Ser Trp Val Ser Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Val Ser Gly Tyr Thr Phe
        35                  40                  45

Thr Asp His Ile Ile His Trp Met Lys Gln Arg Pro Glu Gln Gly Leu
50                  55                  60

Glu Trp Ile Gly Tyr Ile Tyr Pro Arg Asp Gly Tyr Ile Lys Tyr Asn
65                  70                  75                  80

Tyr Phe Cys Ala Arg Gly Tyr Tyr Tyr Ala Met Asp Tyr Trp Gly Gln
                85                  90                  95

Glu Lys Phe Lys Gly Lys Ala Thr Leu Thr Ala Asp Lys Ser Ser Ser
            100                 105                 110

Thr Ala Tyr Met Gln Val Asn Ser Leu Thr Ser Glu Asp Ser Ala Val
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160
```

```
Leu Gly Cys Leu Val Lys Gly Tyr Phe Pro Glu Pro Val Thr Val Thr
                165                 170                 175
Trp Asn Ser Gly Ser Leu Ser Ser Gly Val His Thr Phe Pro Ala Val
            180                 185                 190
Leu Gln Ser Asp Leu Tyr Thr Leu Ser Ser Val Val Thr Val Pro Ser
        195                 200                 205
Ser Thr Trp Pro Ser Gln Thr Val Thr Cys Asn Val Ala His Pro Ala
    210                 215                 220
Ser Ser Thr Lys Val Asp Lys Lys Ile Val Pro Arg Asp Cys Gly Cys
225                 230                 235                 240
Lys Pro Cys Ile Cys Thr Val Pro Glu Val Ser Ser Val Phe Ile Phe
                245                 250                 255
Pro Pro Lys Pro Lys Asp Val Leu Thr Ile Thr Leu Thr Pro Lys Val
            260                 265                 270
Thr Cys Val Val Val Asp Ile Ser Lys Asp Asp Pro Glu Val Gln Phe
        275                 280                 285
Ser Trp Phe Val Asp Asp Val Glu Val His Thr Ala Gln Thr Gln Pro
    290                 295                 300
Arg Glu Glu Gln Phe Asn Ser Thr Phe Arg Ser Val Ser Glu Leu Pro
305                 310                 315                 320
Ile Met His Gln Asp Trp Leu Asn Gly Lys Glu Phe Lys Cys Arg Val
                325                 330                 335
Asn Ser Ala Ala Phe Pro Ala Pro Ile Glu Lys Thr Ile Ser Lys Thr
            340                 345                 350
Lys Gly Arg Pro Lys Ala Pro Gln Val Tyr Thr Ile Pro Pro Pro Lys
        355                 360                 365
Glu Gln Met Ala Lys Asp Lys Val Ser Leu Thr Cys Met Ile Thr Asp
    370                 375                 380
Phe Phe Pro Glu Asp Ile Thr Val Glu Trp Gln Trp Asn Gly Gln Pro
385                 390                 395                 400
Ala Glu Asn Tyr Lys Asn Thr Gln Pro Ile Met Asp Thr Asp Gly Ser
                405                 410                 415
Tyr Phe Val Tyr Ser Lys Leu Asn Val Gln Lys Ser Asn Trp Glu Ala
            420                 425                 430
Gly Asn Thr Phe Thr Cys Ser Val Leu His Glu Gly Leu His Asn His
        435                 440                 445
His Thr Glu Lys Ser Leu Ser His Ser Pro Gly Lys
    450                 455                 460

<210> SEQ ID NO 39
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Lys Leu Pro Val Arg Leu Leu Val Leu Met Phe Trp Ile Pro Ala
1               5                   10                  15
Ser Arg Ser Asp Val Leu Met Thr Gln Thr Pro Leu Ser Leu Pro Val
            20                  25                  30
Ser Leu Gly Asp Gln Ala Ser Ile Ser Cys Arg Ser Ser Gln Ser Ile
        35                  40                  45
Val His Ser Ile Gly Asn Thr Tyr Leu Glu Trp Tyr Leu Gln Lys Pro
```

```
                50                  55                  60
Gly Gln Ser Pro Lys Leu Leu Ile Tyr Lys Val Ser Asn Arg Phe Ser
 65                  70                  75                  80

Gly Val Pro Glu Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Tyr Trp Met His
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Ile Asp Pro Ser Asp Val Tyr Thr Asn Tyr Asn Pro Lys Phe Lys
1               5                  10                  15

Gly

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Tyr Ser Gly Asp Tyr
1               5
```

<210> SEQ ID NO 43
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Leu Gln Pro Gly Ala Glu Leu Val Arg Pro Gly Thr
1               5                   10                  15

Ser Val Lys Leu Ser Cys Lys Thr Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Met Ile Asp Pro Ser Asp Val Tyr Thr Asn Tyr Asn Pro Lys Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Ser Gly Asp Tyr Trp Gly Gln Gly Thr Thr Leu Thr
            100                 105                 110

Val Ser Ser
        115

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
            100                 105                 110

<210> SEQ ID NO 45
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Trp Ser Cys Ile Ile Val Leu Leu Val Ser Thr Ala Thr Cys

-continued

```
1               5                   10                  15
Val His Ser Gln Val Gln Leu Leu Gln Pro Gly Ala Glu Leu Val Arg
            20                  25                  30
Pro Gly Thr Ser Val Lys Leu Ser Cys Lys Thr Ser Gly Tyr Thr Phe
            35                  40                  45
Ser Ser Tyr Trp Met His Trp Val Lys Gln Arg Pro Gly Gln Gly Leu
            50                  55                  60
Glu Trp Ile Gly Met Ile Asp Pro Ser Asp Val Tyr Thr Asn Tyr Asn
65                  70                  75                  80
Pro Lys Phe Lys Gly Lys Ala Thr Leu Thr Val Asp Thr Ser Ser Ser
                    85                  90                  95
Thr Ala Tyr Met Gln Leu Ser Ser Leu Thr Ser Glu Asp Ser Ala Val
                    100                 105                 110
Tyr Tyr Cys Ala Arg Asn Tyr Ser Gly Asp Tyr Trp Gly Gln Gly Thr
                    115                 120                 125
Thr Leu Thr Val Ser Ser Ala Lys Thr Thr Pro Pro Ser Val Tyr Pro
            130                 135                 140
Leu Ala Pro Gly Ser Ala Ala Gln Thr Asn Ser Met Val Thr Leu Gly
145                 150                 155                 160
Cys Leu Val Lys Gly Tyr Phe Pro Glu Pro Val Thr Val Thr Trp Asn
                    165                 170                 175
Ser Gly Ser Leu Ser Ser Gly Val His Thr Phe Pro Ala Val Leu Gln
                    180                 185                 190
Ser Asp Leu Tyr Thr Leu Ser Ser Ser Val Thr Val Pro Ser Ser Thr
                    195                 200                 205
Trp Pro Ser Gln Thr Val Thr Cys Asn Val Ala His Pro Ala Ser Ser
            210                 215                 220
Thr Lys Val Asp Lys Lys Ile Val Pro Arg Asp Cys Gly Cys Lys Pro
225                 230                 235                 240
Cys Ile Cys Thr Val Pro Glu Val Ser Ser Val Phe Ile Phe Pro Pro
                    245                 250                 255
Lys Pro Lys Asp Val Leu Thr Ile Thr Leu Thr Pro Lys Val Thr Cys
                    260                 265                 270
Val Val Val Asp Ile Ser Lys Asp Asp Pro Glu Val Gln Phe Ser Trp
                    275                 280                 285
Phe Val Asp Asp Val Glu Val His Thr Ala Gln Thr Gln Pro Arg Glu
            290                 295                 300
Glu Gln Phe Asn Ser Thr Phe Arg Ser Val Ser Glu Leu Pro Ile Met
305                 310                 315                 320
His Gln Asp Trp Leu Asn Gly Lys Glu Phe Lys Cys Arg Val Asn Ser
                    325                 330                 335
Ala Ala Phe Pro Ala Pro Ile Glu Lys Thr Ile Ser Lys Thr Lys Gly
                    340                 345                 350
Arg Pro Lys Ala Pro Gln Val Tyr Thr Ile Pro Pro Lys Glu Gln
            355                 360                 365
Met Ala Lys Asp Lys Val Ser Leu Thr Cys Met Ile Thr Asp Phe Phe
            370                 375                 380
Pro Glu Asp Ile Thr Val Glu Trp Gln Trp Asn Gly Gln Pro Ala Glu
385                 390                 395                 400
Asn Tyr Lys Asn Thr Gln Pro Ile Met Asp Thr Asp Gly Ser Tyr Phe
                    405                 410                 415
Val Tyr Ser Lys Leu Asn Val Gln Lys Ser Asn Trp Glu Ala Gly Asn
                    420                 425                 430
```

-continued

```
Thr Phe Thr Cys Ser Val Leu His Glu Gly Leu His Asn His His Thr
        435                 440                 445

Glu Lys Ser Leu Ser His Ser Pro Gly Lys
    450                 455

<210> SEQ ID NO 46
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
                100                 105                 110

Phe Gln Gly Ser Tyr Val Pro Trp Thr Phe Gly Gly Gly Thr Lys Leu
            115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
    195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Tyr Gly Met Ser
1               5

<210> SEQ ID NO 48
```

```
<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Ile Asn Thr Tyr Ser Gly Val Pro Thr Tyr Ala Asp Asp Phe Lys
1               5                   10                  15

Gly

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Arg Asp Gly Tyr Gln Val Ala Trp Phe Ala Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Thr Ser Thr Asp Ile Asp Asp Asp Met Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Gly Asn Thr Leu Arg Pro
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gln Ser Asp Asn Leu Pro Tyr Thr
1               5

<210> SEQ ID NO 53
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 53

```
Gln Ile Gln Leu Val Gln Ser Gly Pro Glu Leu Lys Lys Pro Gly Glu
1               5                   10                  15

Ala Val Lys Ile Ser Cys Lys Ser Ser Gly Tyr Thr Phe Thr Thr Tyr
            20                  25                  30

Gly Met Ser Trp Val Lys Gln Ala Pro Gly Arg Ala Leu Lys Trp Met
        35                  40                  45

Gly Trp Ile Asn Thr Tyr Ser Gly Val Pro Tyr Ala Asp Asp Phe
    50                  55                  60

Lys Gly Arg Phe Ala Phe Ser Leu Glu Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Arg Asp Gly Tyr Gln Val Ala Trp Phe Ala Tyr Trp Gly
            100                 105                 110

Gln Gly Thr Leu Val Thr Val Ser Ala
        115                 120
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Glu Thr Thr Val Thr Gln Ser Pro Ala Ser Leu Ser Met Ala Ile Gly
1               5                   10                  15

Asp Lys Val Thr Ile Arg Cys Ile Thr Ser Thr Asp Ile Asp Asp Asp
            20                  25                  30

Met Asn Trp Phe Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Gly
    50                  55                  60

Ser Gly Tyr Gly Thr Asp Phe Ile Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105
```

<210> SEQ ID NO 55
<211> LENGTH: 464
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Ala Val Lys Ile Ser Cys Lys Ser Ser Gly Tyr Thr Phe
        35                  40                  45

Thr Thr Tyr Gly Met Ser Trp Val Lys Gln Ala Pro Gly Arg Ala Leu
```

```
            50                  55                  60
Lys Trp Met Gly Trp Ile Asn Thr Tyr Ser Gly Val Pro Thr Tyr Ala
 65                  70                  75                  80

Asp Asp Phe Lys Gly Arg Phe Ala Phe Ser Leu Glu Ser Ser Ala Ser
                 85                  90                  95

Thr Ala Tyr Leu Gln Ile Asn Asn Leu Lys Asn Glu Asp Thr Ala Thr
            100                 105                 110

Tyr Phe Cys Ala Arg Gly Arg Asp Gly Tyr Gln Val Ala Trp Phe Ala
            115                 120                 125

Tyr Trp Gly Gln Gly Thr Leu Val Thr Val Ser Ala Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
            165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
            195                 200                 205

Thr Val Pro Ser Ser Thr Trp Pro Ser Gln Thr Val Thr Cys Asn Val
210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
            245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
            275                 280                 285

Glu Val Gln Phe Ser Trp Phe Val Asp Asp Val Glu Val His Thr Ala
290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
            325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
            405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
            435                 440                 445

Leu His Asn His His Thr Glu Lys Ser Leu Ser His Ser Pro Gly Lys
            450                 455                 460

<210> SEQ ID NO 56
```

```
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Phe Ser Leu Ala Leu Leu Ser Leu Leu Leu Cys Val Ser
1               5                   10                  15

Asp Ser Arg Ala Glu Thr Thr Val Thr Gln Ser Pro Ala Ser Leu Ser
            20                  25                  30

Met Ala Ile Gly Asp Lys Val Thr Ile Arg Cys Ile Thr Ser Thr Asp
        35                  40                  45

Ile Asp Asp Asp Met Asn Trp Phe Gln Gln Lys Pro Gly Glu Pro Pro
50                  55                  60

Lys Leu Leu Ile Ser Glu Gly Asn Thr Leu Arg Pro Gly Val Pro Ser
65                  70                  75                  80

Arg Phe Ser Gly Ser Gly Tyr Gly Thr Asp Phe Ile Phe Thr Ile Glu
                85                  90                  95

Asn Met Leu Ser Glu Asp Val Ala Asp Tyr Tyr Cys Leu Gln Ser Asp
            100                 105                 110

Asn Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Tyr Trp Met His
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58
```

```
Met Ile Asp Pro Ser Asp Ser Tyr Thr Asn Tyr Asn Pro Lys Phe Lys
1               5                   10                  15

Gly
```

<210> SEQ ID NO 59
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Met Ile Asp Pro Ser Asp Ser Tyr Thr Asn Tyr Asn Pro Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Tyr Ser Gly Asp Tyr Trp Gly Gln Gly Thr Thr Leu Thr
            100                 105                 110

Val Ser Ser
        115
```

<210> SEQ ID NO 60
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
            100                 105                 110
```

<210> SEQ ID NO 61
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Met Gly Trp Ser Cys Ile Ile Val Leu Leu Val Ser Thr Ala Thr Gly
1               5                   10                  15

Val His Ser Gln Val Gln Leu Gln Gln Pro Gly Ala Glu Leu Val Arg
            20                  25                  30

Pro Gly Thr Ser Val Lys Leu Ser Cys Lys Ala Ser Gly Tyr Thr Phe
        35                  40                  45

Thr Asn Tyr Trp Met His Trp Val Lys Gln Arg Pro Gly Gln Gly Leu
    50                  55                  60

Glu Trp Ile Gly Met Ile Asp Pro Ser Asp Ser Tyr Thr Asn Tyr Asn
65                  70                  75                  80

Pro Lys Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asn Tyr Ser Gly Asp Tyr Trp Gly Gln Gly Thr
        115                 120                 125

Thr Leu Thr Val Ser Ser Ala Lys Thr Thr Pro Pro Ser Val Tyr Pro
130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Thr
        195                 200                 205

Trp Pro Ser Gln Thr Val Thr Cys Asn Val Ala His Pro Ala Ser Ser
    210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335

Ala Ala Phe Pro Ala Pro Ile Glu Lys Thr Ile Ser Lys Thr Lys Gly
            340                 345                 350

Arg Pro Lys Ala Pro Gln Val Tyr Thr Ile Pro Pro Lys Glu Gln
        355                 360                 365

Met Ala Lys Asp Lys Val Ser Leu Thr Cys Met Ile Thr Asp Phe Phe
370                 375                 380

Pro Glu Asp Ile Thr Val Glu Trp Gln Trp Asn Gly Gln Pro Ala Glu
385                 390                 395                 400
```

```
Asn Tyr Lys Asn Thr Gln Pro Ile Met Asp Thr Asp Gly Ser Tyr Phe
            405                 410                 415

Val Tyr Ser Lys Leu Asn Val Gln Lys Ser Asn Trp Glu Ala Gly Asn
            420                 425                 430

Thr Phe Thr Cys Ser Val Leu His Glu Gly Leu His Asn His His Thr
            435                 440                 445

Glu Lys Ser Leu Ser His Ser Pro Gly Lys
            450                 455

<210> SEQ ID NO 62
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```